(12) United States Patent  (10) Patent No.: US 8,073,104 B2
Yan et al.  (45) Date of Patent: Dec. 6, 2011

(54) PORTAL AND REAL TIME IMAGING FOR TREATMENT VERIFICATION

(75) Inventors: Di Yan, Auburn Hills, MI (US); Jian Liang, Troy, MI (US); Alvaro Martinez, Bloomfield Hills, MI (US)

(73) Assignee: William Beaumont Hospital, Royal Oak, MI (US)

( * ) Notice: Subject to any disclaimer, the term of this patent is extended or adjusted under 35 U.S.C. 154(b) by 153 days.

(21) Appl. No.: 12/556,270

(22) Filed: Sep. 9, 2009

(65) Prior Publication Data
US 2010/0119032 A1 May 13, 2010

Related U.S. Application Data

(63) Continuation-in-part of application No. 11/805,716, filed on May 24, 2007.

(60) Provisional application No. 61/214,539, filed on Apr. 24, 2009, provisional application No. 60/808,343, filed on May 25, 2006, provisional application No. 61/881,092, filed on Jan. 18, 2007.

(51) Int. Cl.
*A61N 5/10* (2006.01)
(52) U.S. Cl. ....................................... 378/65
(58) Field of Classification Search .............. 378/4–20, 378/62, 65, 901; 382/128, 130–132
See application file for complete search history.

(56) References Cited

U.S. PATENT DOCUMENTS

| | | | |
|---|---|---|---|
| 5,602,892 A | 2/1997 | Llacer | |
| 5,699,805 A | 12/1997 | Seward et al. | |
| 5,754,622 A | 5/1998 | Hughes | |
| 6,389,104 B1 | 5/2002 | Bani-Hashemi et al. | |
| 6,393,096 B1 | 5/2002 | Carol et al. | |
| 6,546,073 B1 | 4/2003 | Lee | |
| 6,560,311 B1 | 5/2003 | Shepard et al. | |
| 6,661,870 B2 | 12/2003 | Kapatoes et al. | |
| 6,865,254 B2 | 3/2005 | Näfstadius | |
| 6,915,005 B1 | 7/2005 | Ruchala et al. | |
| 2003/0191363 A1 | 10/2003 | Boll et al. | |
| 2004/0002641 A1 | 1/2004 | Sjogren et al. | |
| 2004/0081270 A1 | 4/2004 | Heuscher | |
| 2004/0096033 A1 | 5/2004 | Seppi et al. | |
| 2004/0120452 A1 | 6/2004 | Shapiro et al. | |
| 2004/0254448 A1 | 12/2004 | Amies et al. | |
| 2005/0027196 A1 | 2/2005 | Fitzgerald | |
| 2005/0054937 A1 | 3/2005 | Takaoka et al. | |
| 2005/0080336 A1 | 4/2005 | Byrd et al. | |
| 2005/0085710 A1 | 4/2005 | Earnst et al. | |

(Continued)

OTHER PUBLICATIONS

Yan D., et al., "A New Model for 'Accept or Reject' Strategies in On-Line and Off-Line Treatment Evaluation," International Journal of Radiation Oncology, Biology Physics, vol. 31, No. 4, 1995, pp. 943-952.

(Continued)

*Primary Examiner* — Courtney Thomas
(74) *Attorney, Agent, or Firm* — Brinks Hofer Gilson & Lione

(57) ABSTRACT

A system for radiotherapy includes a first imaging system and a second imaging system. The first imaging system generates projection images of an area of interest of an object, and the second imaging system generates portal images of the area of interest of the object synchronously with the generation of the projection images. The radiotherapy system further includes a processing system that receives data associated with the projection images and data associated with the portal images and reconstructs 3D and 4D portal images from the projection images and the portal images.

20 Claims, 17 Drawing Sheets

U.S. PATENT DOCUMENTS

| | | | |
|---|---|---|---|
| 2005/0111621 | A1 | 5/2005 | Riker et al. |
| 2005/0197564 | A1 | 9/2005 | Dempsey |
| 2006/0017009 | A1 | 1/2006 | Rink et al. |
| 2006/0259282 | A1 | 11/2006 | Failla et al. |
| 2006/0269049 | A1 | 11/2006 | Yinn et al. |
| 2006/0274885 | A1 | 12/2006 | Wang et al. |
| 2006/0285639 | A1 | 12/2006 | Olivera et al. |
| 2006/0285640 | A1 | 12/2006 | Nizin et al. |
| 2007/0003123 | A1 | 1/2007 | Fu et al. |
| 2007/0016014 | A1 | 1/2007 | Hara et al. |
| 2007/0280408 | A1 | 12/2007 | Zhang |

OTHER PUBLICATIONS

Yan D., et al., "Adaptive Radiation Therapy," Phys. Med. Biol., vol. 42, 1997, pp. 123-132.

Yan D., et al., "The Use of Adaptive Radiation Therapy to Reduce Setup Error: A Prospective Clinical Study," Int. J. Radiation Oncology Biol. Phys., vol. 41, No. 3, 1998, pp. 715-720.

Yan D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.

Yan D., et al., "A Model to Accumulate Fractionated Dose in a Deforming Organ," Int. J. Radiation Oncology Biol. Phys., vol. 44, No. 3, 1999, pp. 665-675.

Lockman D., et al., "Estimating the Dose Variation in a Volume of Interest with Explicit Consideration of Patient Geometric Variation," Med. Phys., vol. 27, No. 9, Sep. 2000, pp. 2100-2108.

Yan D., et al., "An Off-Line Strategy for Constructing a Patient-Specific Planning Target Volume for Image Guided Adaptive Radiotherapy of Prostate Cancer," Int. J. Radiation Oncology Biol. Phys., vol. 48, No. 1, 2000, pp. 289-302.

Yan D., "Treatment Strategy for Daily Image Feedback Adaptive Radiotherapy," Proceeding, XIIIth International Conference on the Use of Computers in Radiotherapy, Heidelberg, Germany, 2000, pp. 518-520.

Yan D. et al. "Organ/Patient Geometric Variation in External Beam Radiotherapy and Its Effect," Med. Phys., vol. 28, No. 4, Apr. 2001, pp. 593-602.

Yan D., et al., Strategies for Off-Line and On-Line Image Feedback Adaptive Radiotherapy, Editors: BK Paliwal, DE Herbert, JF Fowler, MP Mehta, Biological & Physical Basis of IMRT & Tomotherapy, AAPM Symposium Proceeding No. 12, 2002, pp. 139-150.

Birkner M., et al., "Adapting Inverse Planning to Patient and Organ Geometrical Variation: Algorithm and Implementation," Med. Phys., vol. 30, No. 10, Oct. 2003, pp. 2822-2831.

Liang J., et al., "Reducing Uncertainties in Volumetric Image Based Deformable Organ Registration," Med. Phys., vol. 30, No. 8, Aug. 2003, pp. 2116-2122.

Ghilezan M., et al., "Online Image-Guided Intensity-Modulated Radiotherapy for Prostate Cancer: How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Weinberg R.., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.

Söhn M. et al., "Modeling Individual Geometric Variation Based on Dominant Eigenmodes of Organ Deformation: Implementation and Evaluation," Phys Med Biol, vol. 50, 2005, pp. 5893-5908.

Yan D., et al "Computed Tomography Guided Management of Interfractional Patient Variation," Semin. Radiat. Oncol. vol. 15, 2005, pp. 168-179.

Yan D., "Image-Guided/Adaptive Radiotherapy," Medical Radiology-Radiation Oncology, Volume: New Technologies in Radiation Oncology, Edited by W. Schlegel, T. Bortfeld and Al Grosu, Springer-Verlag, Berlin, Heidelberg, New York, Hong Kong, Sep. 8, 2005, ISBN 3-540-00321-5, pp. 317-332.

Chen, J., et al., "Dose-Guided Radiation Therapy with Megavoltage Cone-Beam CT," published by the British Journal of Radiology, vol. 79, 2006, pp. S87-S98.

Chi Y., et al., "A Material Sensitivity Study on the Accuracy of Deformable Organ Registration Using Linear Biomechanical Models," Med. Phys., vol. 33: No. 2, Feb. 2006, pp. 421-433.

Kessler, M.L., "Image Registration and Data Fusion in Radiation Therapy," The British Journal of Radiology, vol. 79, 2006, pp. S99-S108.

Yan D., "Image-Guided Adaptive Radiotherapy Model," AAPM, Mar. 10, 2006, pp. 1-15.

Zhang T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.

Kapatoes, J.M., et al., "On the Accuracy and Effectiveness of Dose Reconstruction for Tomotherapy," Phys. Med. Biol., vol. 46, 2001, pp. 943-966.

Schaly, B., et al., "Tracking the Dose Distribution in Radiation Therapy by Accounting for Variable Anatomy," Phys. Med. Biol., vol. 49, 2004, pp. 791-805.

Yong, Y., et al., "Evaluation of On-Board kV Cone Beam CT (CBCT)-based Dose Calculation," Phys. Med. Biol., vol. 52, 2007, pp. 685-705.

Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication source unknown, (publication date unknown), 4 pages, while the date of publication is unknown, it is believe that the article was publicly available before May 24, 2007.

Yan D., "Adapt Radiotherapy to Temporal Biological Targets Assessed Using Biological Images," publication source unknown, while the date of publication is unknown, it is believe that the article was publicly available before May 24, 2007, 3 pages.

Yan D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.

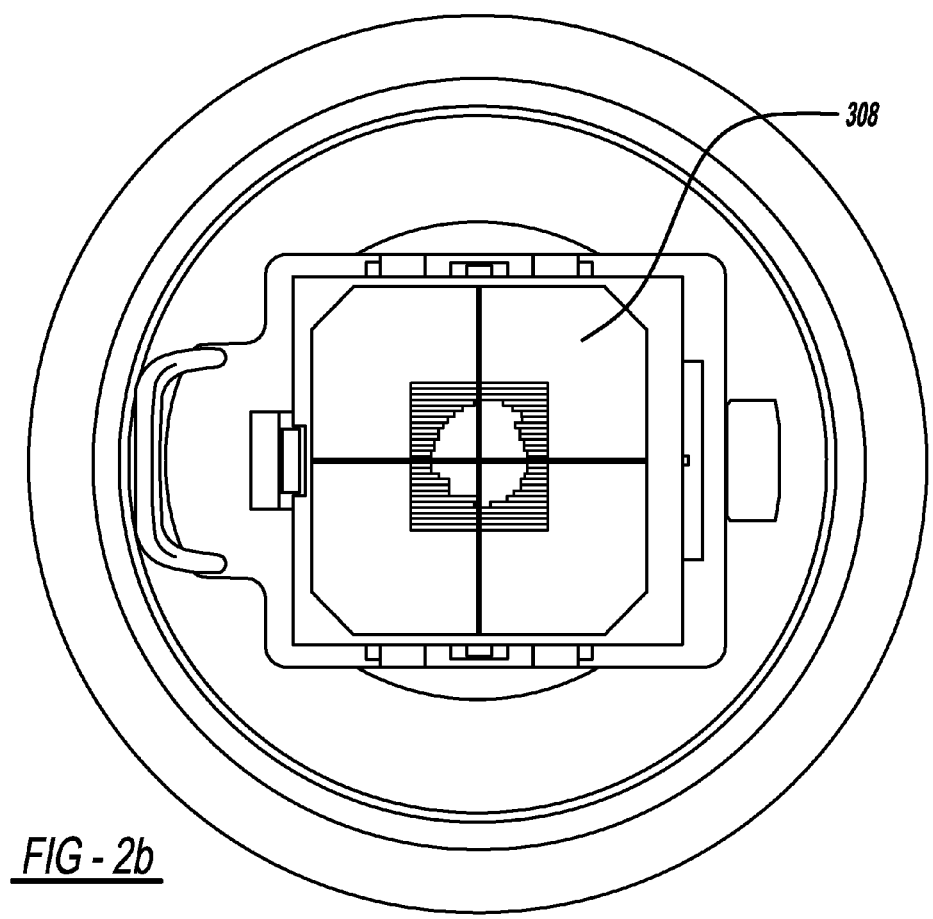
*FIG - 2b*
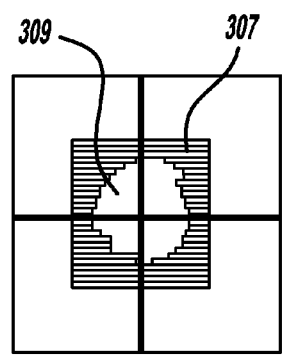 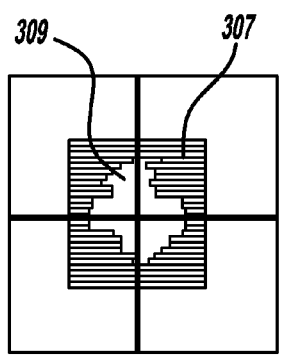 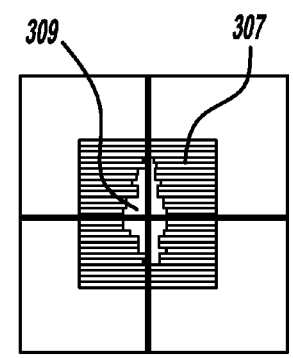
*FIG - 2c*　　　*FIG - 2d*　　　*FIG - 2e*

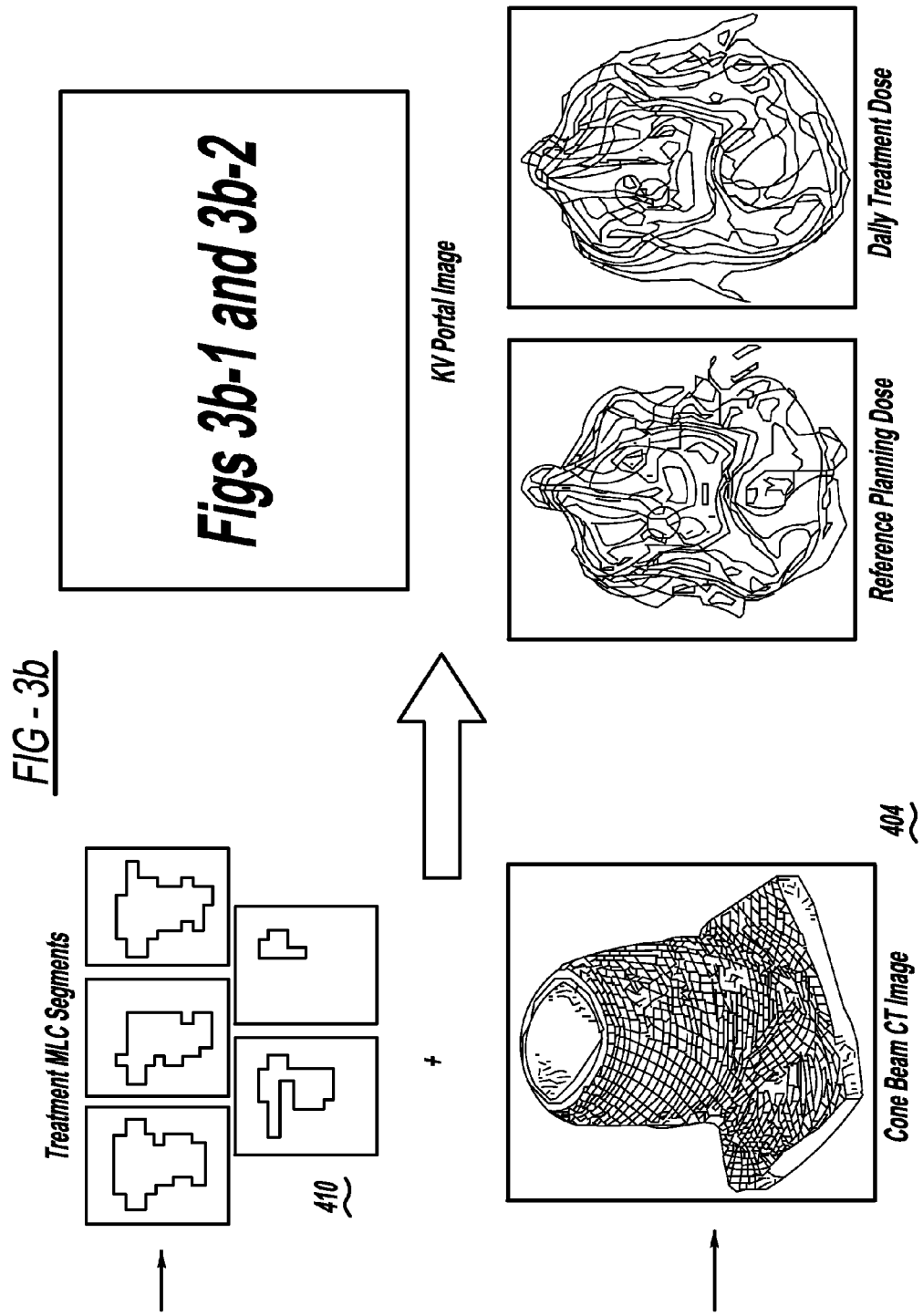

PORTAL AND REAL TIME IMAGING FOR TREATMENT VERIFICATION

RELATED APPLICATIONS

This application claims the benefit of U.S. Provisional Application No. 61/214,539, filed Apr. 24, 2009, and is a continuation-in-part of U.S. application Ser. No. 11/805,716, filed May 24, 2007, which claims the benefit of U.S. Provisional Application No. 60/808,343, filed May 25, 2006, and U.S. Provisional Application No. 60/881,092, filed Jan. 18, 2007, the entire contents of each of which are incorporated herein by reference.

BACKGROUND

The present invention relates to image guided radiotherapy. Presently, online treatment dose construction and estimation include portal ex-dose reconstruction to reconstruct treatment dose on a conventional linear accelerator. Specifically, the exit dose is measured using an MV portal imager to estimate treatment dose in the patient. However, this method has not been employed for patient treatment dose construction, since the dose reconstruction method lacks patient anatomic information during the treatment, and the scattered exit dose is difficult to calibrate properly.

In the past, a single pre-treatment computed tomography scan has been used to design a patient treatment plan for radiotherapy. Use of such a single pre-treatment scan can lead to a large planning target margin and uncertainty in normal tissue dose due to patient variations, such as organ movement, shrinkage and deformation, that can occur from the start of a treatment session to the end of the treatment session. For the foregoing reasons, there is a need in the radiotherapy field for a new and improved imaging system.

BRIEF SUMMARY

In satisfying the above need, as well as overcoming the enumerated drawbacks and other limitations of the related art, the present invention provides an improved radiation detection device.

A system for radiotherapy includes a first imaging system and a second imaging system. The first imaging system generates projection images of an area of interest of an object, and the second imaging system generates portal images of the area of interest of the object synchronously with the generation of the projection images. The radiotherapy system further includes a processing system that receives data associated with the projection images and data associated with the portal images and reconstructs 3D and 4D portal images from the projection images and the portal images.

One or more aspects of the invention may provide the advantage of providing online and offline treatment dose reconstruction, and a treatment decision tool that provides real-time, on-line and off-line treatment evaluation and on-line or off-line modification of a reference plan.

Other advantages and features will become apparent from the following description and from the claims.

BRIEF DESCRIPTION OF THE DRAWINGS

In the accompanying drawings the components are not necessarily to scale, emphasis instead being placed upon illustrating the principles of the invention. Moreover, like reference numerals designate corresponding parts throughout the views. In the drawings:

FIGS. 2a-2e shows an embodiment of an onboard imaging system and/or radiation therapy systems to be used with the radiation therapy system of FIG. 1 for performing dose tracking and feedback in accordance with the invention;

DETAILED DESCRIPTION OF THE INVENTION

Figure 1:
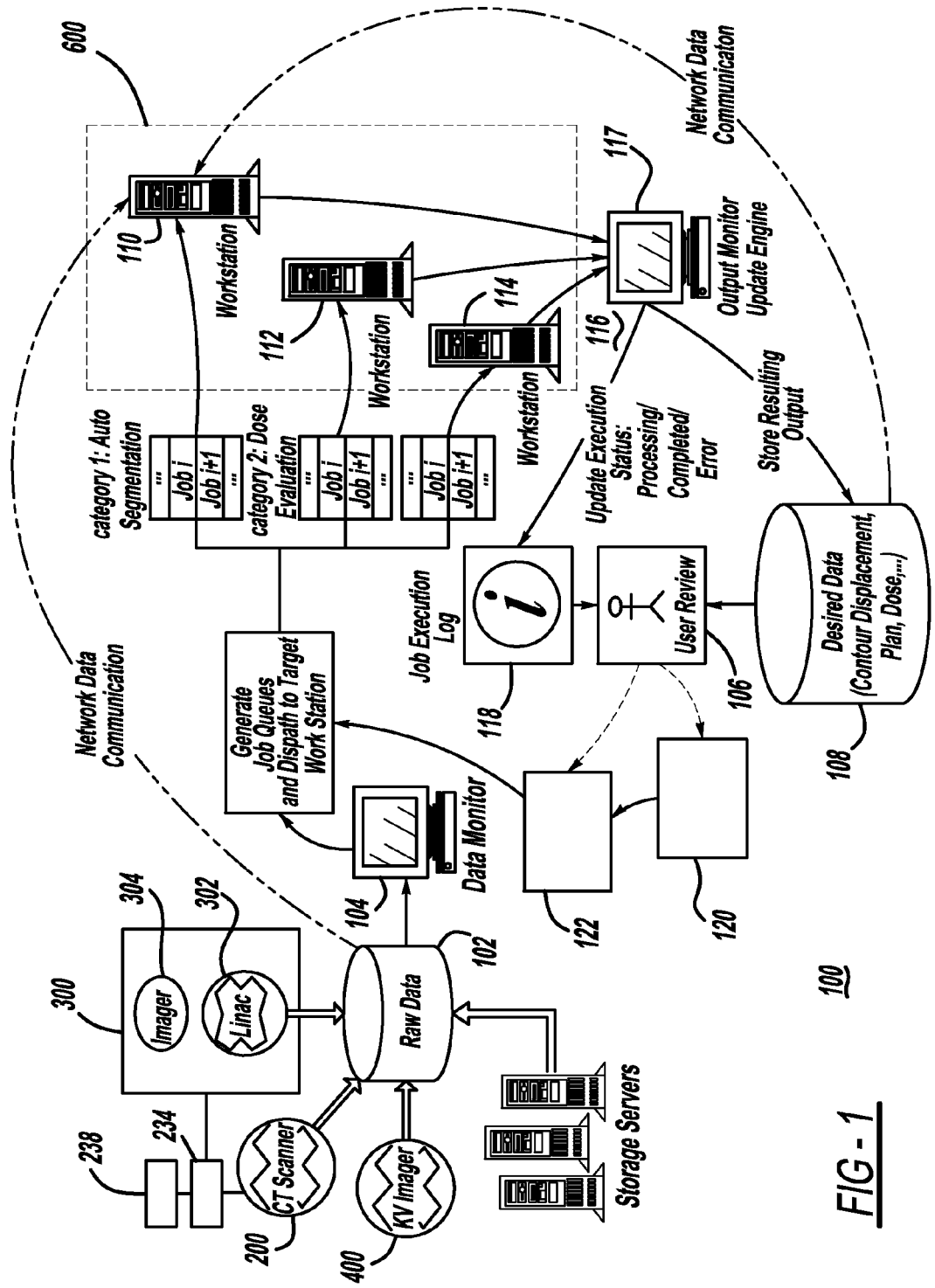
FIG. 1 schematically shows an embodiment of a radiation therapy system that employs a dose tracking and feedback process and a possible workflow for auto-construction, estimation and evaluation of cumulative treatment dose, and patient anatomy and dose feedback for adaptive planning optimization in accordance with the present invention.

Referring now to FIG. 1, generally illustrated therein is a schematic view of a volumetric image guided adaptive radiotherapy system, such as cone-beam computerized tomography (CBCT) image guided adaptive radiotherapy (IGART) system 100, and a corresponding workflow sequence for auto-construction and evaluation of daily cumulative treatment dose are shown in FIGS. 1-6, wherein like elements are denoted by like numerals. As shown in FIG. 1, the CBCT IGART system 100 includes a number of major systems: 1) a three-dimensional volumetric imaging system, such as an x-ray cone-beam computed tomography system 200, 2) a megavoltage (MeV) imaging system 300 that includes a radiation therapy source, such as a linear accelerator 302, and an imager 304, 3) a kilovoltage (kV) portal imager processor/software system 400 and 4) a treatment dose tracking and feedback system 600, each of which are discussed below.

Three-Dimensional Volumetric Imaging System

Mechanical operation of a cone-beam computed tomography system 200 is similar to that of a conventional computed tomography system, with the exception that an entire volumetric image is acquired through less than two rotations (preferably one rotation) of the source and detector. This is made possible by the use of a two-dimensional (2-D) detector, as opposed to the one-dimensional (1-D) detectors used in conventional computed tomography.

An example of a known cone-beam computed tomography imaging system is described in U.S. Pat. No. 6,842,502, the entire contents of which are incorporated herein by reference. The patent describes an embodiment of a cone-beam computed tomography imaging system that includes a kilovoltage x-ray tube and a flat panel imager having an array of amorphous silicon detectors. As a patient lies upon a treatment table, the x-ray tube and flat panel image rotate about the patient in unison so as to take a plurality of images as described previously.

Figure 2A:
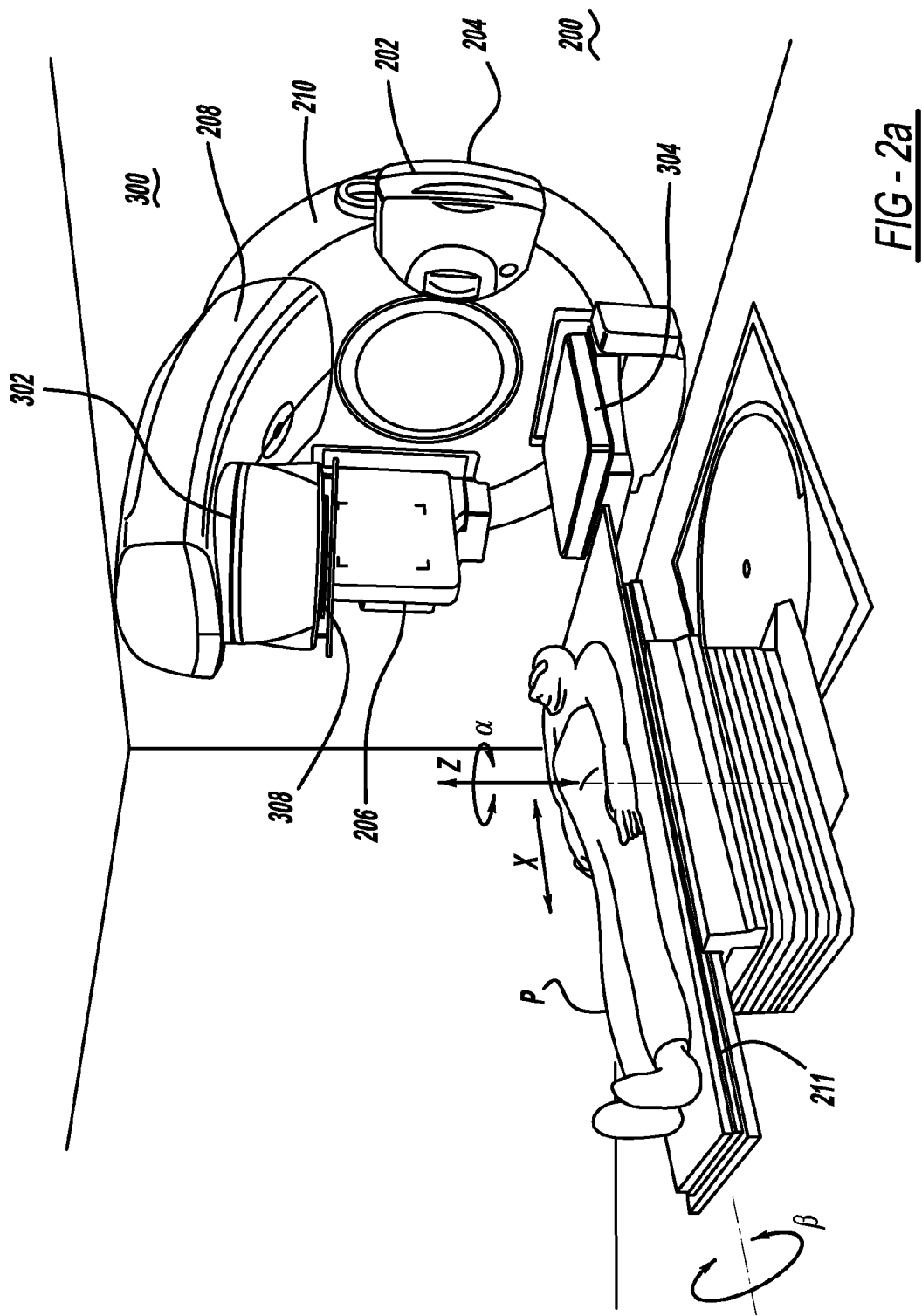
Figure 3A:
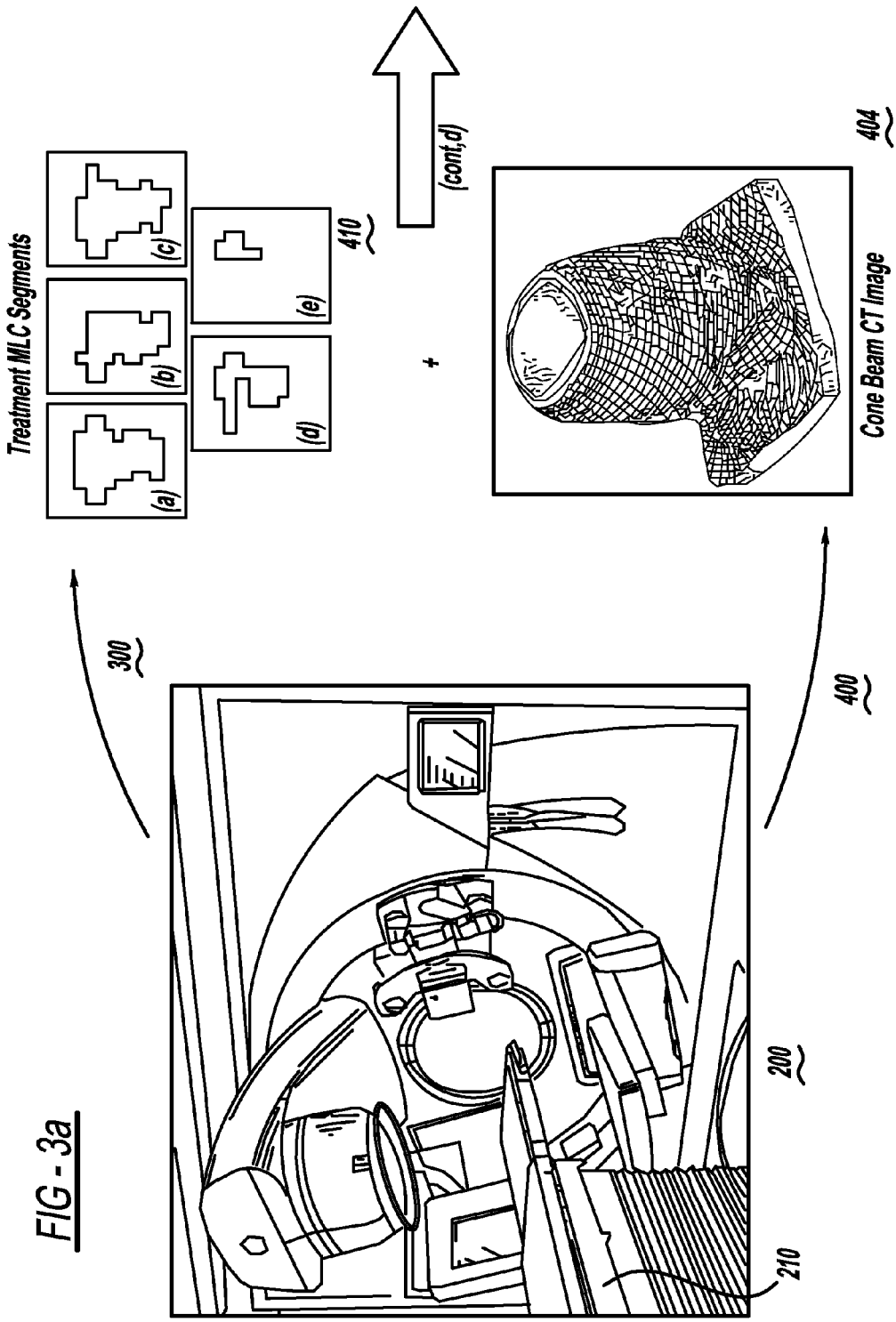
FIGS. 3a-b provides a visual representation of a possible process to form a kV portal image.
Figures 1, 3B:
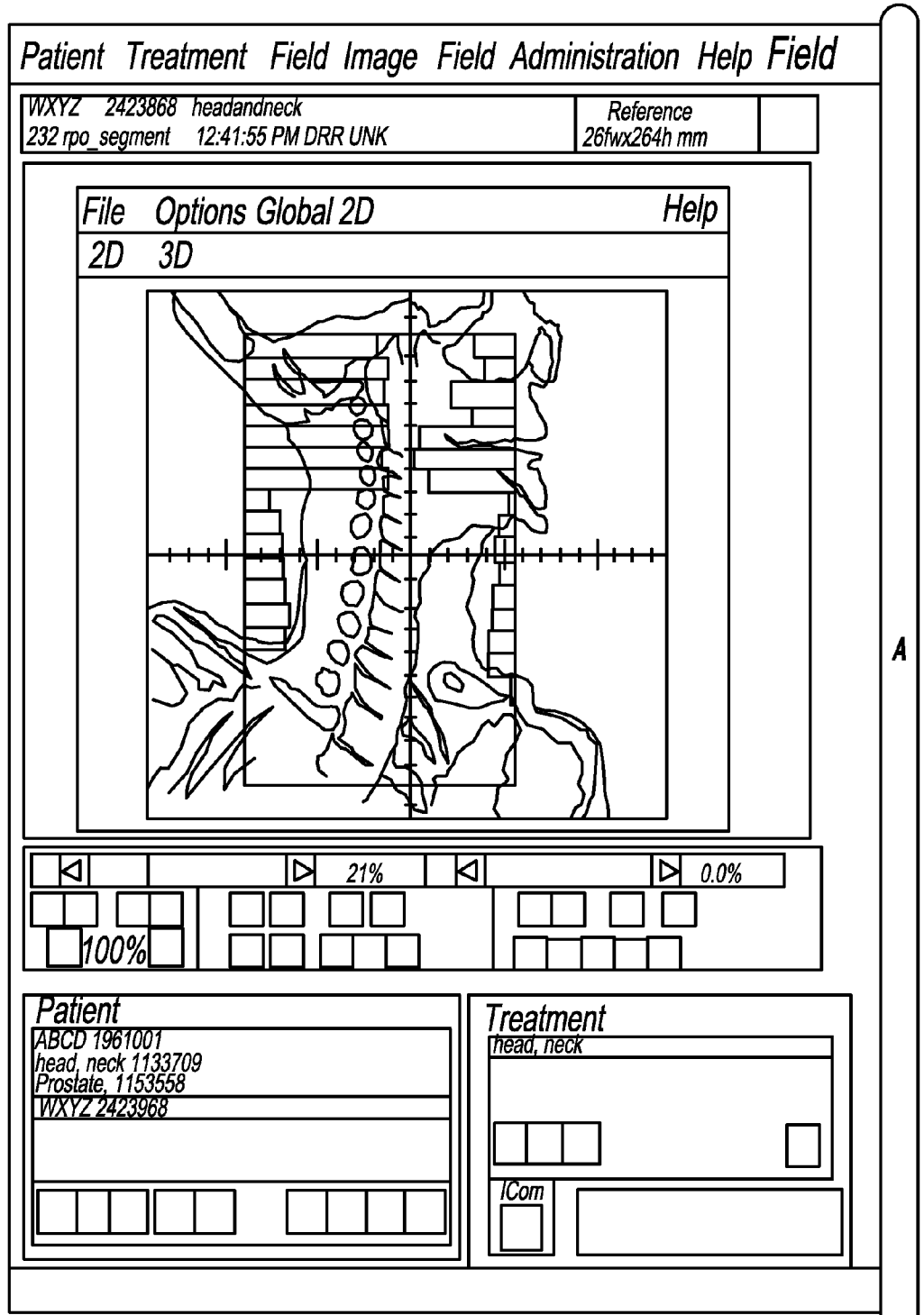
Figures 2, 3B:
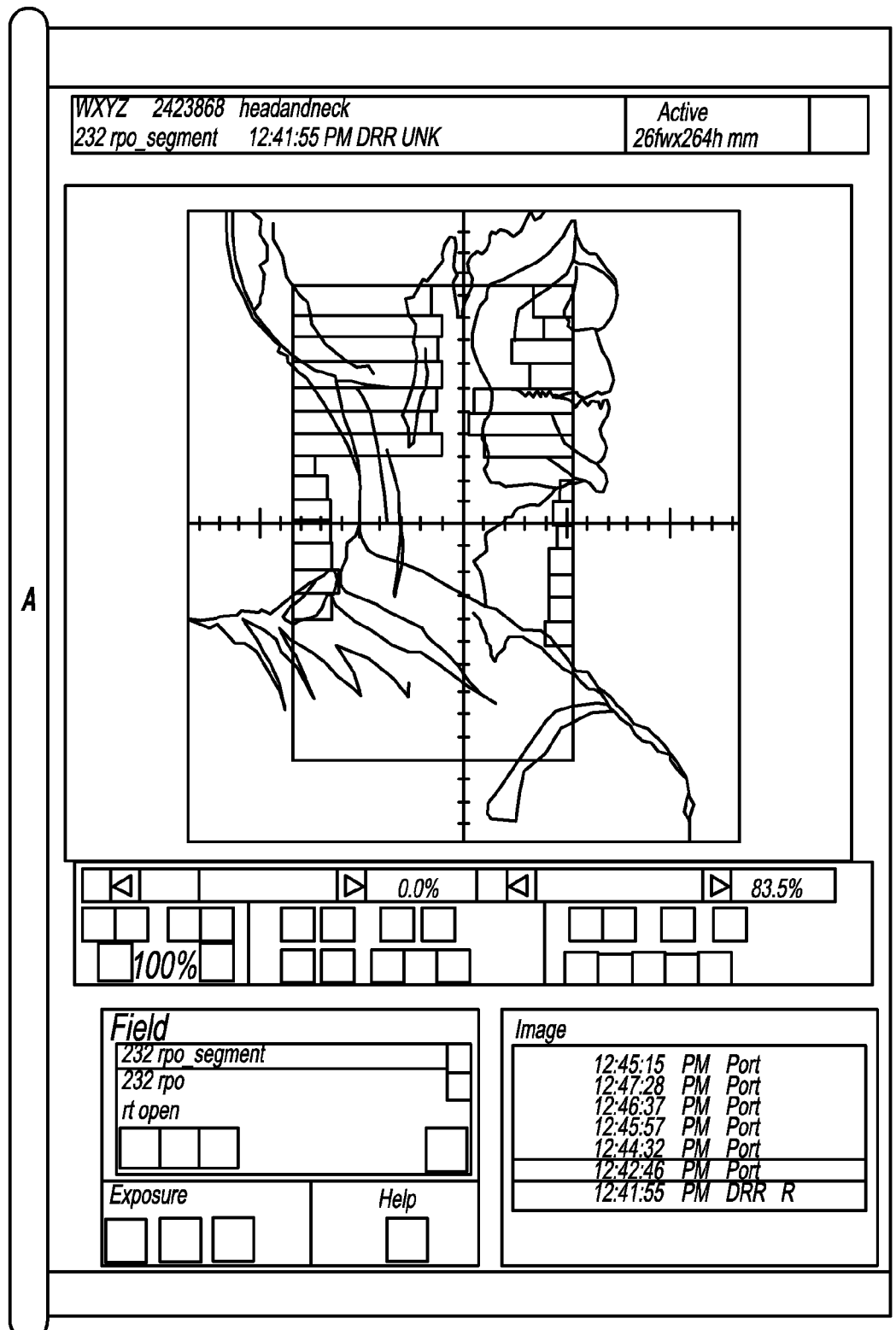

As shown in FIG. 2, a volumetric imaging systems is illustrated. In particular, FIG. 2a shows an embodiment of a wall-mounted cone-beam computed tomography system 200 and MeV portal imaging system 300 that can be adapted to be used with the cone-beam computed tomography and megavoltage portal imaging system sold under the trade name Synergy by Elekta of Crawley, the United Kingdom. Such systems 200 and 300 are described in pending U.S. patent application Ser. No. 11/786,781, entitled "Scanning Slot Cone-Beam Computed Tomography and Scanning Focus Spot Cone-Beam Computed Tomography" and filed on Apr. 12, 2007, the entire contents of which are incorporated herein by reference.

The cone-beam computed tomography system 200 includes an x-ray source, such as x-ray tube 202, a rotary collimator 204 and a flat-panel imager/detector 206 mounted on a gantry 208. As shown in FIG. 2a, the flat-panel imager 206 can be mounted to the face of a flat, circular, rotatable drum 210 of the gantry 208 of a medical linear accelerator 302, where the x-ray beam produced by the x-ray tube 202 is approximately orthogonal to the treatment beam produced by the radiation therapy source 302.

Note that the detector 206 can be composed of a two-dimensional array of semiconductor sensors that may be each made of amorphous silicon (α-Si:H) and thin-film transistors. The analog signal from each sensor is integrated and digitized. The digital values are transferred to the data storage server 102.

After the fan beams from collimator 204 traverse the width of a patient P and impinge on the entire detector 206 in the manner described above, computer 234 instructs the drum 210 to rotate causing the x-ray source 202, the collimator 204 and the detector 206 rotate about the patient P to another position so that the scanning process described above can be repeated and another two-dimensional projection is generated. The above rotation of the x-ray source 202, collimator 204 and detector 206 is continued until a sufficient number of two-dimensional images are acquired for forming a cone-beam computed tomography image. Less than two rotations should be needed for this purpose (images formed from a rotation of less than 360° can be formed as well). The two-dimensional projections from each position are combined in the computer 234 to generate a three-dimensional image to be shown on display 236 in a manner similar to that of the cone-beam computed tomography systems described previously.

As shown in FIG. 2, the system 300 includes a separate radiation therapy x-ray source, such as a linear source 302 and a detector/imager 304 that are separately mounted to the rotating drum 210. The source 302 operates at a power level higher than that of x-ray tube 202 so as to allow for treatment of a target volume in a patient lying on a movable table 211 (movable in x, y and z-direction via computer 234). The linear source 302 generates a beam of x-rays or particles, such as photons, protons or electrons, which have an energy ranging from about 4 MeV to about 25 MeV.

As mentioned above, the particles are used to treat a specific area of interest of a patient, such as a tumor. Prior to arriving at the area of interest, the beam of particles is shaped by adjusting multiple leafs 307 (FIGS. 2c-e) to have a particular cross-sectional area 309 via a multi-leaf collimator 308. The cross-sectional area 309 is chosen so that the beam of particles interacts with the area of interest to be treated and not areas of the patient that are healthy. The radiation penetrating through the area of interest can be imaged via imager 304 in a well known manner.

Treatment Dose Tracking and Feedback System

As shown in FIG. 1, the treatment dose tracking and feedback system 600 includes a workstation or data server 110 that includes processors dedicated to perform a segmentation/registration process on a three-dimensional, volumetric image of a patient received from server 102 that was generated by cone-beam computed tomography system 200. The workstation 110 is able to identify and register each volume of image data within each volumetric image. Such identification and registration allows for the same volume of image data to be tracked in position from one therapy session to another therapy session.

Figure 6:
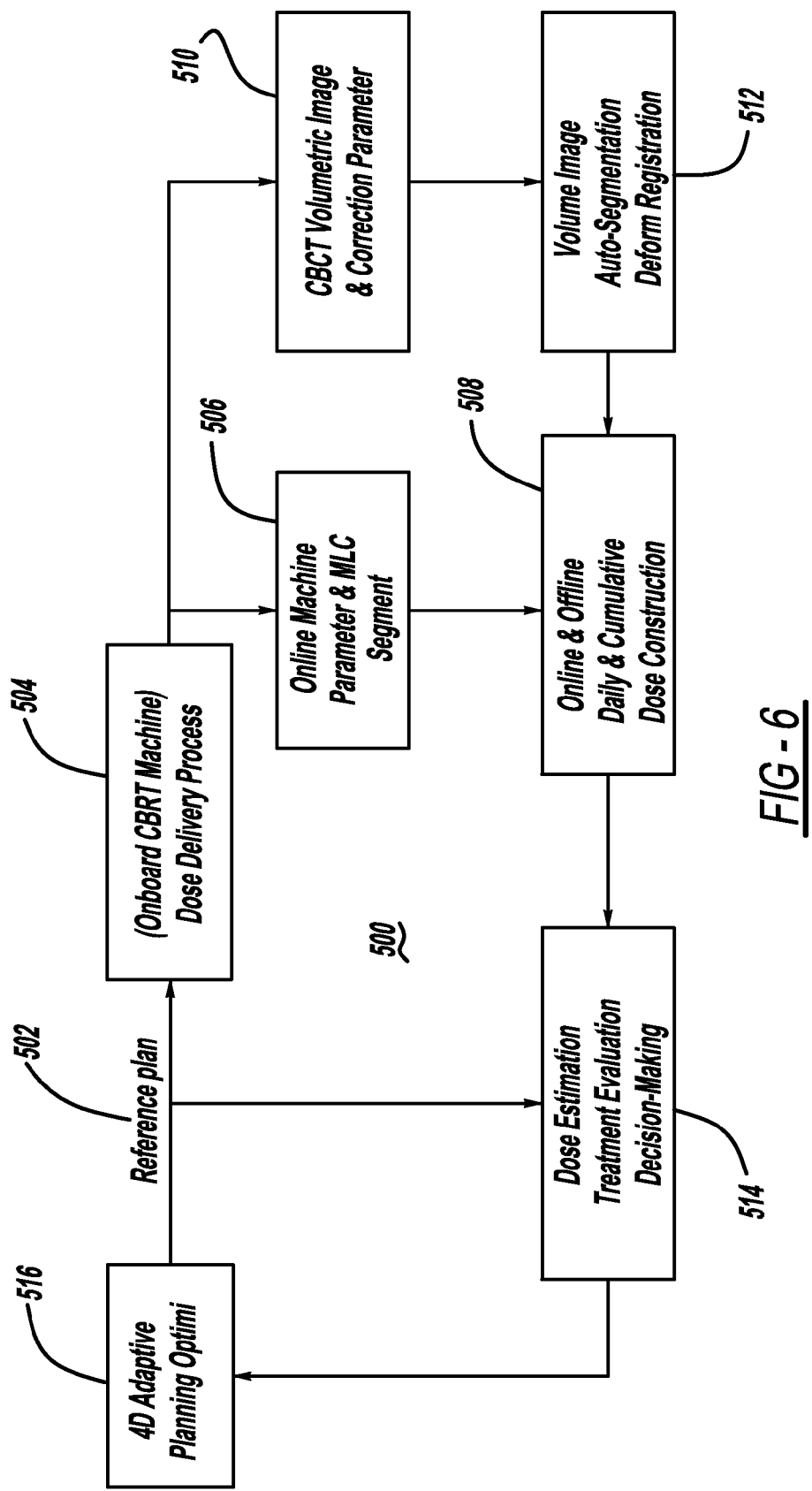
FIG. 6 shows an embodiment of a radiotherapy process to be used with the systems of FIGS. 1 and 2.

The treatment dose tracking and feedback system 600 further includes a workstation or data server 112 that includes processors dedicated to perform a treatment dose construction process based on 1) the segmentation/registration process performed by workstation 110 and 2) parameters of the beam of radiation emitted from the source 302 as it impinges on the patient that are measured and stored in server 102, such as angular position, beam energy and cross-sectional shape of the beam, in accordance with a reference plan 502 (FIG. 6). Such parameters can be in the form of the angular position of the gantry 208, the angular orientation of the collimator 308, the positions of the leaves of the multi-leaf collimator 308, position of the table 211 and energy of the radiation beam. Once the position and shape of a subvolume of image data is known, the treatment dosage received by that very same subvolume can be determined/constructed based on the above mentioned parameters of the beam of radiation emitted from the source 302 as it impinges on the patient. Such a determination is made for each of the subvolumes of image data for each of the volumetric images generated by system 200.

The treatment dose tracking and feedback system 600 further includes a workstation or data server 114 that includes processors dedicated to perform a an adaptive planning process that can either 1) adjust the radiation therapy treatment for the particular day in a real-time manner based on off-line and on-line information or 2) adjust a radiation therapy treatment plan in a non-real-time manner based on off-line information. The adjustment is based on how the dose calculated by the workstation 112 differs from dose preferred by the treatment plan. Note that the term "real-time" refers to the time period when the radiation therapy source is activated and treating the patient. The term "on-line" regards when a patient is on the treatment table and "off-line" refers to when the patient is off the treatment table.

In summary, the treatment dose tracking and feedback system 600 can perform real time treatment dose construction and 4D adaptive planning based on volumetric image information and therapy beam parameters that are measured in a real time manner during a therapy session. The system 600 can also perform adaptive planning in a non-real-time manner as well. Such real time and non-real time processes will be discussed in more detail with respect to the process schematically shown in FIG. 6. Note that in an alternative embodiment, the workstations 110, 112 and 114 can be combined into a single workstation wherein the processes associated with workstations 110, 112 and 114 are performed by one or more processors. Note that the real time treatment dose construction determined by workstation 112 and the 4D adaptive planning determined by workstation 114 can be displayed on a monitor 117 of Quality Assurance (QA) evaluation station 116. Based on the information displayed on monitor 117, medical personnel can alter, if required, the calculated 4D adaptive plan so as to be within acceptable parameters. Thus, the QA evaluation station 116 acts as a way to ensure confidence in future real time changes made to the therapy session.

In this scenario, the QA evaluation station 116 and the treatment dose tracking and feedback system 600 can be collectively thought of as a 4D planning and control system.

With the above description of the onboard cone-beam computed tomography system 200, megavoltage imaging and radiation therapy system 300, QA evaluation station 116 and the treatment dose tracking and feedback system 600 in mind, the operation of the CBCT IGART system 100 of FIG. 1 can be understood. In particular, the previously described online volumetric imaging information and real time therapy beam parameters are captured from systems 200, 300 and 400 and stored in data storage server 108. The volumetric imaging information and therapy beam parameters are then sent to data monitor job controller 104 that automatically assigns tasks, based on pre-designed treatment schedule and protocol, to each of the work stations 110, 112 and 114 and controls the accomplishment of such tasks. The tasks are stored in temporal job queues 124 for dispatching, based on clinical priorities, to each of the workstations 110, 112 and 114. The clinical priority can be reassigned from a clinical user's request 122 based on the treatment review and evaluation on the physician evaluation/decision making station 106. In addition, the station 106 also provides commands for treatment/plan modification decisions. The modification server 120 receives commands from the station 106 and modifies the ongoing treatment plan, beam or patient position on the system 300 based on the optimized adaptive plan created from the adaptive planning workstation 114.

As shown in FIG. 1, the raw data from server 108 is also sent to a workstation 110. The workstation 110 is dedicated to perform an autosegmentation/registration process on a three-dimensional, volumetric image of a patient generated by cone-beam computed tomography system 200. The raw data from server 108 is also sent to workstation 112 and workstation 114. Workstation 112 performs daily and cumulative treatment dose construction/evaluation from the raw data. Workstation 114 performs adaptive planning from the raw data. These three workstations 110, 112 and 114 perform their tasks automatically with order of their job queues 126, 128 and 130, respectively. The above described segmentation/registration, treatment dose construction/evaluation and adaptive planning will be described later with respect to the process schematically shown in FIG. 6.

As shown in FIG. 1, the segmentation/registration, treatment dose construction and adaptive planning information generated from workstations 110, 112 and 114 is sent to the QA evaluation station 116 which interacts with a clinical user to verify and modify, if necessary, the results from the above workstations 110, 112 and 114. The output from QA evaluation station 116 is then stored in derived data server 108.

The QA station 116 provides an update execution status to job execution log server 118 that supplies information whether processing of information is presently occurring, whether processing is completed or whether an error has occurred. Whenever a task of treatment dose construction or adaptive planning modification is completed by workstations 112 and 114, respectively, the evaluation station 116 provides treatment evaluation information which includes both the current treatment status and the completed treatment dose and outcome parameters estimated based on the patient and treatment data from previous treatments. The user at QA evaluation station 116 can then provide commands or a new clinical schedule to the high priority job request server 122 to either request new information or modify clinical treatment schedule. In addition, the user can also make decisions to execute a new adaptive plan or perform a treatment/patient position correction through the server 120.

The CBCT IGART system 100 performs a number of processes, including a kV portal imaging process via kV portal imaging processor/software 400 and a an image guided adapted radiation therapy process 500, both of which will be described below with respect to FIGS. 3-6.

Pre-Treatment Process

As an example of how the radiation therapy process proceeds, assume a patient who has undergone previous radiation therapy sessions at a clinic has another session scheduled for a particular day. The patient arrives at the clinic on the scheduled day and proceeds to the therapy room similar to that shown in FIG. 3a. The therapy room includes the cone-beam computed tomography system 200 and MeV portal imaging system 300 previously described with respect to FIG. 2a. The patient lies on the table 211 and is prepared for the on-line therapy session by the medical staff ("on-line" being defined as events and processes performed as the patient is positioned on the radiation therapy treatment table 211).

Figure 4:
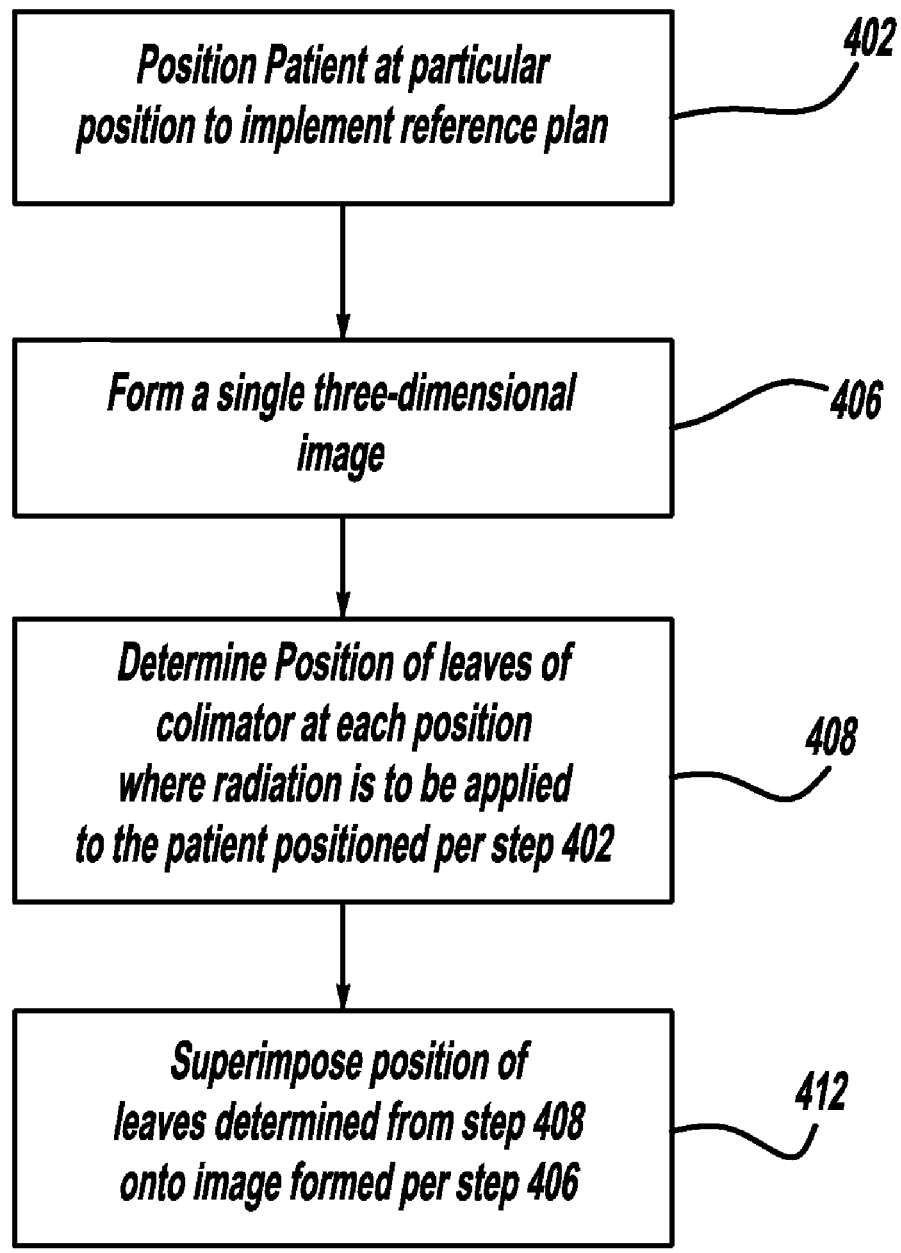
FIG. 4 is a flow diagram of a sequence of steps for forming either of the kV portal images of FIGS. 3 and 5.
Figure 5A:
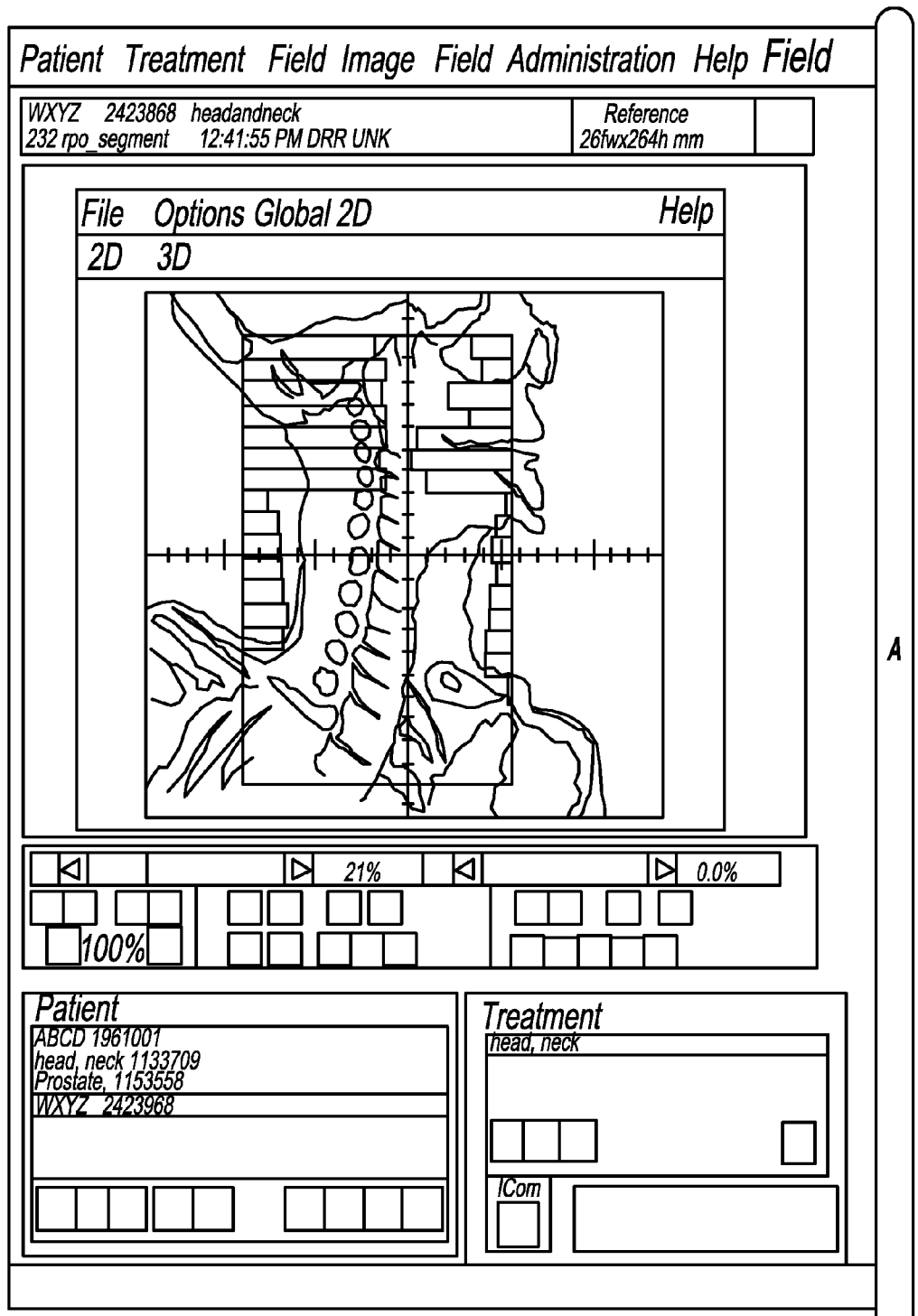
FIG. 5 shows a reference image and a kV portal image with a beam eye view of organs of interest.
Figure 5B:
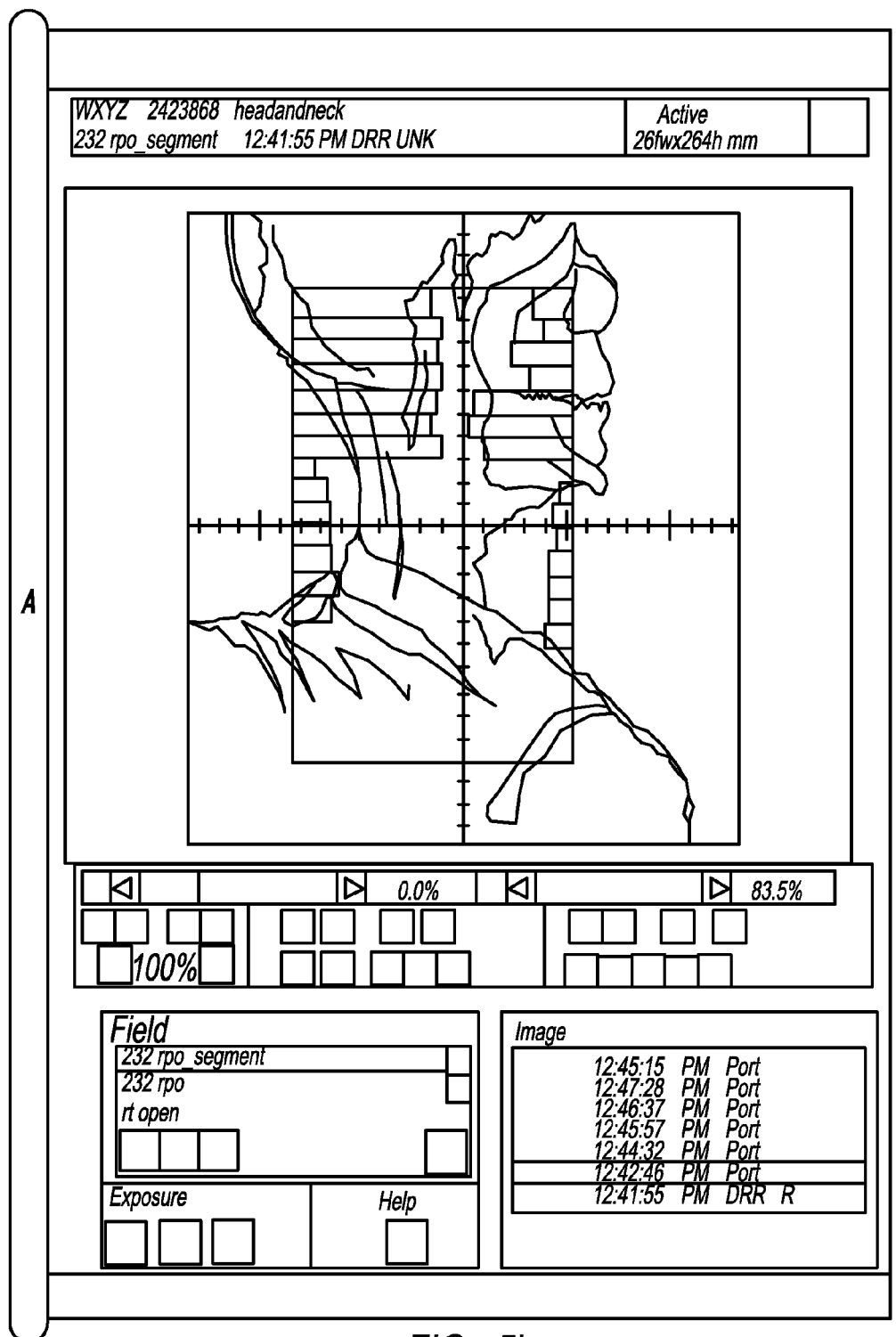

At this point of time, a reference treatment plan for applying therapeutic radiation to the patient has previously been determined for the patient based on the previous radiation therapy sessions. A reference treatment plan is designed before the treatment delivery based on the most likely planning volumetric image of the area of interest to be treated. The reference treatment plan contains patient setup position, therapy machine parameters and expected daily and cumulative doses to be applied to various areas of the patient. Such a reference plan specifies the area(s) of the patient to be exposed to radiation and the dosage the area(s) are to receive from the radiation source during a single session. Thus, the reference plan will include information regarding the beam angle/gantry position, beam energy and cross-sectional area of the beam formed by the multi-leaf collimator 308. Based on the reference plan, the patient is instructed to move to a particular position, such as on his or her side, that is optimal for applying radiation to the area of interest within the patient per the reference plan. While at the particular position, a pre-treatment kV portal imaging process employing kV processor/software 400 is performed prior to the radiation therapy session. The pre-treatment kV portal imaging process is schematically shown in FIGS. 3-5. In particular, the process includes forming a two-dimensional projection/radiographic image from the cone-beam computed tomographic image 404 of the patient prior to treatment, wherein the image 404 contains the area of interest while the patient is at the particular position on the table 211 per step 406 of the process. According to the reference plan, the radiation source 302 is to be moved to one or more positions to apply radiation at each position while the patient is at the particular position. At each position of the radiation source 302, the leaves of the multi-leaf collimator 308 are to be moved to form a desired outline for forming the radiation beam to a particular cross-sectional shape. The positions of the leaves at each position of the radiation source are determined, per step 408, as schematically represented by the multi-leaf outlines 410 of FIGS. 3a-b.

The cone-beam computed tomographic image 404 of the area of interest while the patient is at the particular position and the positions of the leaves/outlines 410 are then stored and processed in a processor of workstation 110 as shown in FIGS. 3b, 4, and 5. Such processing involves, per step 412, superimposing each outline 410 on a two-dimensional projection/radiographic image based on the cone-beam image 404 to form a treatment beam eye (BEV) view kV portal image such as shown in FIGS. 3b and 5. Note that the kV portal image can be formed as a kV digital reconstructed radiographic (DRR) image for static patient anatomy verification or as a digital reconstructed fluoroscopic (DRF) image for verification of dynamic patient anatomy motion, such as respiratory motion. In either case, each kV portal image with corresponding outline 410 (FIG. 4*b*, for example) is compared with a treatment reference radiographic image (FIG. 4*a*, for example) that is generated according to the real-time radiation therapy plan to be executed. Should one or more areas of interest, such as a tumor or organ, of the kV portal image be displaced by at least a predetermined amount relative to the position of the corresponding area of interest of the reference image, then steps are taken to adjust the real-time radiation therapy plan for the day's treatment session. If the displacement is below the predetermined amount, then the real-time radiation plan is not adjusted.

In addition to the treatment dose, kV portal image can also be constructed for treatment recordation and verification as shown in FIGS. 3*a-b*. Further, organs of interest manifested on the CBCT image are auto-segmented and registered to the pre-treatment CT image. Therefore, daily and cumulative dose-volume relationships of each organ of interest can be created. In some implementations, a numerical filter is employed to estimate the final treatment dose in each organ of interest by performing parameter estimation for both stationary and non-stationary random processes of patient anatomical variation. Methods for sample estimation, such as the least square estimation, the principal component analysis (PCA) based estimation and singular value decomposition (SVD) estimation, may be implemented.

The estimation is then used to provide information for the treatment evaluation and plan modification decision to determine when to switch on the adaptive planning modification engine.

On-Line, Off-Line Image Guided Adaptive Radiation Therapy Planning

After the kV imaging process is completed, resulting in the initial radiation therapy plan being modified or retained, the patient is repositioned to receive radiation therapy per the modified/original reference plan and image guided adapted radiation therapy process 500 is performed as schematically shown in FIG. 6. In particular, the reference plan 502 is applied to the linear source 302 per process 504 so as to move the source 302 to a position designated in the reference plan 502 and to format parameters of the beam of radiation emitted from the source 302 as it impinges on the patient, such as angular position, beam energy and cross-sectional shape of the beam, in accordance with the reference plan 502. Such on-line and real-time parameters can be in the form of the angular position of the gantry 208, the angular orientation of the collimator 308, the positions of the leaves of the multi-leaf collimator 308, position of the table 211 and energy of the radiation beam. Process 504 can also involve moving individual leaves of a multi-leaf collimator 304 to desired positions per reference plan 502 so that the radiation therapy beam generated by the linear source 302 is collimated so as to radiate a particular shaped area of the patient per the reference plan 502.

Once the reference plan 502 is implemented per process 504, the reference plan 502 can be altered to account for various factors that occur during the radiation therapy session. For example, the process 500 can entail having the system 100 monitor real-time, on-line machine treatment parameters of the linear source 302 and its radiation output online per process 506. The process 506 entails monitoring treatment parameters, such as beam angle, beam energy and cross-sectional shape of the beam. Such parameters can entail the position of the gantry, the angular position of the collimator 308, position of the leaves of the multi-leaf collimator 308, position of the table 211, the energy of the beam.

The real-time, on-line information obtained by the above mentioned monitoring process 506 is fed to workstation 112 of FIG. 1 so that it can be used during either the online and offline daily and cumulative dose construction process 508.

While a radiation therapy beam is applied to the patient per process 504, the area of interest to be treated is imaged via the cone-beam computed tomography system 200. The three-dimensional volumetric image is used to register and track various individual volumes of interest in a real-time and on-line manner. Prior to registration and tracking, a correction parameter must be determined by server 102 per process 510 so as to be applied to the volumetric image. The correction parameter is associated with the fact that rigid body components of the volumetric image are often not oriented in a preferred manner due to a number of factors, such as the position of the patient on the table 211 and the angular position of the collimator. Based on the measurement of those factors, a correction parameter is determined per process 510 that when applied to the three-dimensional image the image is re-oriented to a preferred position. The re-oriented three-dimensional image is stored at workstation 102 of FIG. 1. The workstation 102 contains a library of stored three-dimensional images of one or more areas of interest of the patient.

Once the correction parameter is determined, the segmentation-deformable organ registration workstation 110 receives the volumetric image generated by system 200 and correction parameter from server 102 via process 512. The workstation 110 executes process 512 so as to match the patient anatomical elements manifested on the volumetric image to those on the reference planning volumetric image associated with the reference plan. The image registration results are used to map the pre-treatment organ contours on the planning volumetric image commonly delineated by clinicians, to the corresponding points on the treatment volumetric image automatically. The registration methods applied for this process are quite standard such as the finite element method and the method of image similarity maximization. However, there have been number of modifications performed to optimize these methods for the specific applications of the CBCT image and organs of interest in radiotherapy.

Once each point in the volumetric image is tracked, that information is sent to workstation 112, which also receives the parameters per process 506. At workstation 112, an online daily and cumulative dose construction process 508 is performed. The daily dose construction process entails calculating/constructing for a real-time treatment the dose received for each volume of image data within the volumetric image tracked per process 512. After the treatment session for the day is completed, the daily dose for each volume of image data is stored in server 102. The daily dose for each volume of image data can be combined with daily doses for the same volumes of image data calculated/constructed from previous therapy sessions so that an accumulated dosage over time for each volume of image data is determined per process 508 and stored in server 102.

As shown in FIG. 6, treatment evaluation 514 is performed by workstation 114 following the patient organ registration and treatment dose construction processes 512 and 508, respectively. There are two purposes for treatment evaluation, (a) to determine if the current treatment delivery is the same as the one previously planned for the treatment quality assurance; and (b) to modify the ongoing treatment plan by including the patient anatomy/dose variations observed and quantified so far to optimize the treatment outcome. Such treatment evaluation 514 can be performed real-time, on-line and off-line.

Final treatment dose and outcome estimation are used to provide information for the treatment evaluation and plan modification decision to determine when to switch on the adaptive planning modification engine per process 514 of FIG. 6. A numerical filter is employed to estimate the final treatment dose in each organ of interest by performing parameter estimation for both stationary and non-stationary random processes of patient anatomical variation. Methods for sample estimation, such as the least-square estimation (LSE), the principal component analysis (PCA) based estimation and singular value decomposition (SVD) estimation, are implemented.

The first task of treatment evaluation is related to treatment delivery and plan comparison performed by workstation 112 per process 514. If the comparison shows that the daily or cumulative treatment dosage for a particular subvolume of the image and the corresponding daily or cumulative planned dosages for the corresponding subvolume are outside a certain tolerance, then this means that the reference plan currently being implemented needs to be revised during the present therapy session. Note that the above described daily and cumulative dosages of a subvolume of interest can be tracked/displayed in time, such as on monitor 117 of FIG. 1.

Besides comparing the dosages, the positioning of areas to be treated with respect to the therapeutic beam is tested by forming a kV portal image per the previously described process of FIG. 4. If the real-time kV portal image is compared with a reference portal image and a subvolume of interest of the real-time kV portal image is found to be displaced in position or deformed in shape outside a certain tolerance with respect to a corresponding subvolume position in the reference portal image, then the reference plan, such as adjusting the leaves of the multi-leaf collimator, needs to be changed in this instance as well Note that the above described position of a subvolume of interest can be tracked/displayed in time as shown by a bottom chart of monitor 117 (FIG. 1), wherein x, y and z positions of a particular subvolume is tracked from one daily treatment session to another daily treatment session.

If either of the comparisons described above are outside the corresponding tolerance, then a revision of the reference therapy treatment plan is performed in the on-line or off-line adaptive planning optimization process 516. Adaptive planning optimization is different than conventional radiotherapy planning where only pre-treatment computed tomographic image data is used. Instead, adaptive planning intends to utilize individual treatment history from patient anatomy/dose tracking as feedback to optimize treatment control parameters.

Note that the above-described process regarding FIG. 6 can include real-time data/information by capturing data volumetric image data from system 200 and therapy beam parameter information during the time the therapy beam is generated. Such real-time information can be processed per processes 506, 508, 510, 512 and used in process 514 to determine if the therapy plan should be revised in "real-time." If it is so determined that revision is recommended, then the real-time data/information can be used in conjunction with prior dose information and position/shape information of the volume of interest determined from previous therapy sessions (off-line information) to reformulate the therapy plan.

While the above description demonstrates how "real-time" data/information can be used to revise a therapy plan via the process of FIG. 6, the description is equally applicable to non-real-time adaptive therapy. In this case, processes 506, 508, 510 and 512 use off-line information from previous treatment sessions and process 514 determines if a therapy plan to be used in the future should be revised in "real-time."

In summary, the system 100 and process 500 provide volumetric image guided adaptive radiotherapy, which can be performed in real time, online and offline for treatment dose construction and feedback. Therefore, they provide all possible feedback information for image guided real time, online and offline radiotherapy. Thus, the system 100 and process 500 are able to fully utilize individual treatment information, which primarily includes the patient dose delivered in the previous treatment, patient anatomy in the present treatment and patient anatomy estimated for remaining treatment deliveries.

In another implementation, the kV cone beam projection images on the imager 206 of the CBCT system 204 and the MeV portal images obtained with the imager 304 of the MeV system 300 are at 90° on the treatment gantry. MeV portal images obtained from the imager 304 and kV projection images obtained from the imager 206 provides data for use in constructing 3D and 4D portal images through the use of the processor system described above, to provide images, for example, during treatment of the patient P, patient tissue undergoing time dependent changes, such as through respiration and other dynamic movement during treatment.

Figure 7:
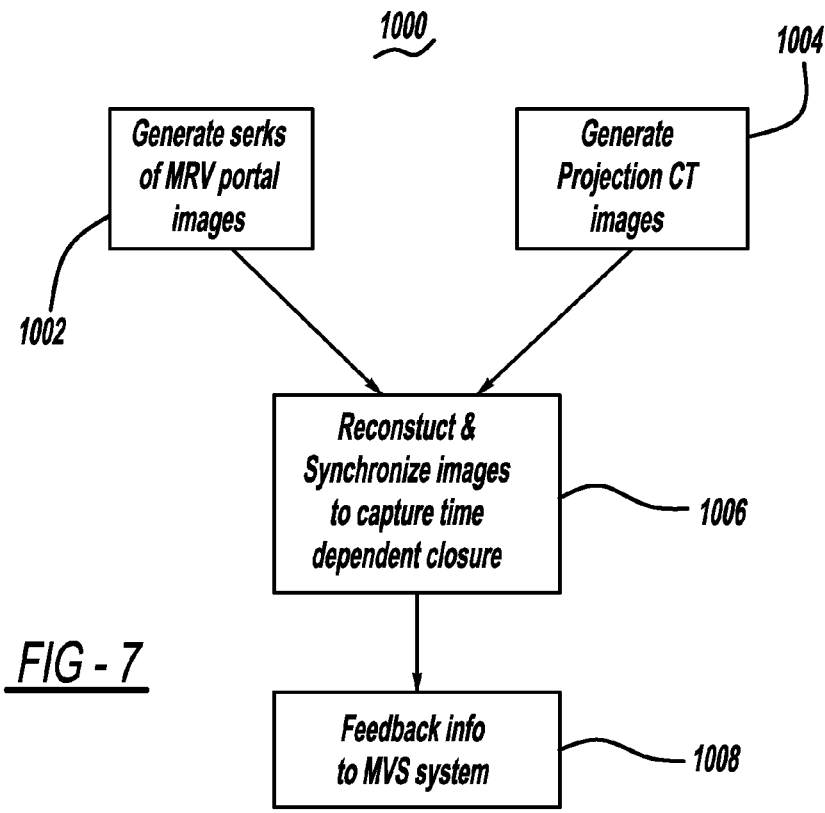
FIG. 7 shows an embodiment of a portal and real-time imaging process to be used with the systems of FIGS. 1 and 2.

With further reference to FIG. 7, a process 1000 illustrates a certain implementation of the system 100. In step 1002, in a single rotation of the MeV system 300, a series of MeV portal images are generated with the imager 304. In step 1004, synchronously, a series of projection CT images are created with the imager 206, which are projection images and are not necessarily reconstructed 3D images. In step 1006, the MeV portal image and the kV projection image data are provided to the aforementioned processor system, which reconstructs projection images of the MV portal images and CT projection image and synchronizes them properly to capture time dependent changes for angle and phase to create 3D and 4D portal images. This allows the clinician to verify appropriate treatment plan by being able to verify dose position as compared with desired target volume during time dependent variations. With this information, in step 1008, the processor system provides feedback to the MeV system 302 to control the beam generated from the system 302. For example, any or all of the energy output from the therapy source 302, the beam shape provided by the collimator 308, and the dose rate may be varied to provide a dynamic delivery control process for the treatment of the patient P.

The constructed 3D and 4D portal images include both patient anatomy and treatment volume and, therefore, provide real time, online and offline treatment verification. Such data can be combined with dynamic ARC delivering technology, such as, for example, volumetric modulated ARC therapy (VMAT) to expand strategies for portal imaging and treatment verification.

In some implementations, multiple beams can be generated with the source 302 to treat two or more separate tumors.

Figure 8A:
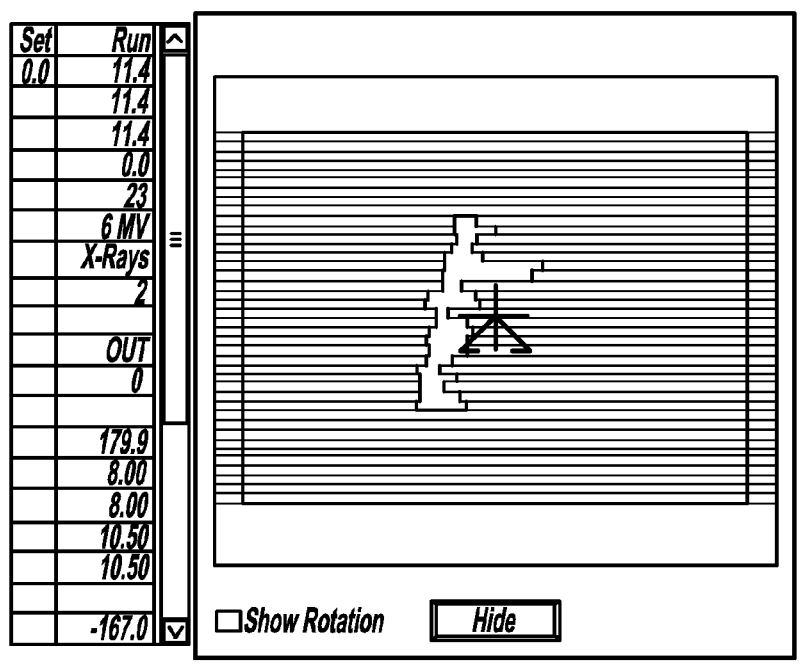
FIGS. 8a-c show real time imaging with verification and dose construction with the use the radiotherapy system of FIGS. 7-9 in accordance with the invention.
Figure 8C:
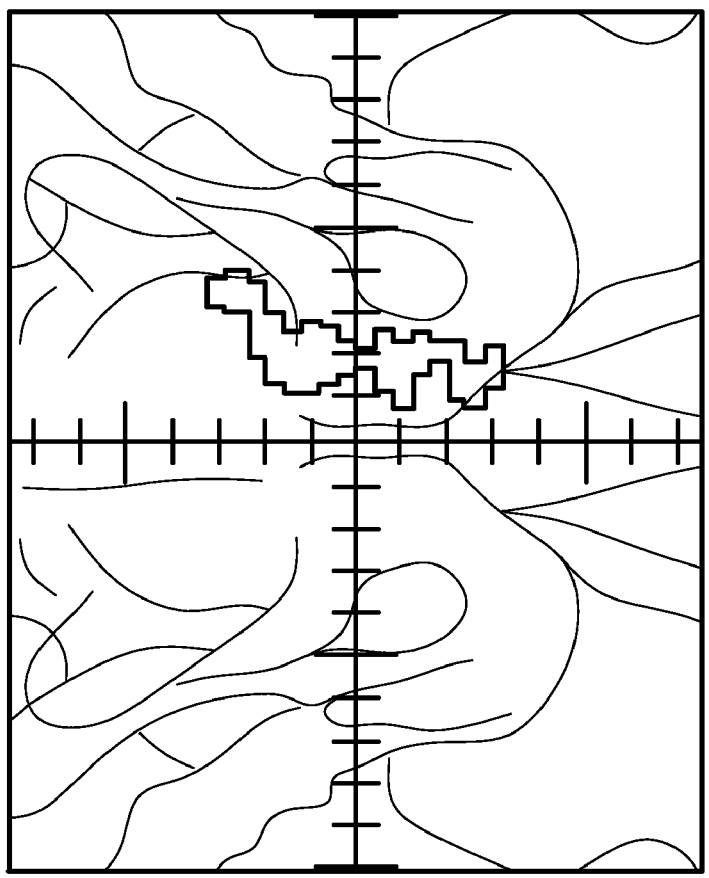
Figure 8B:
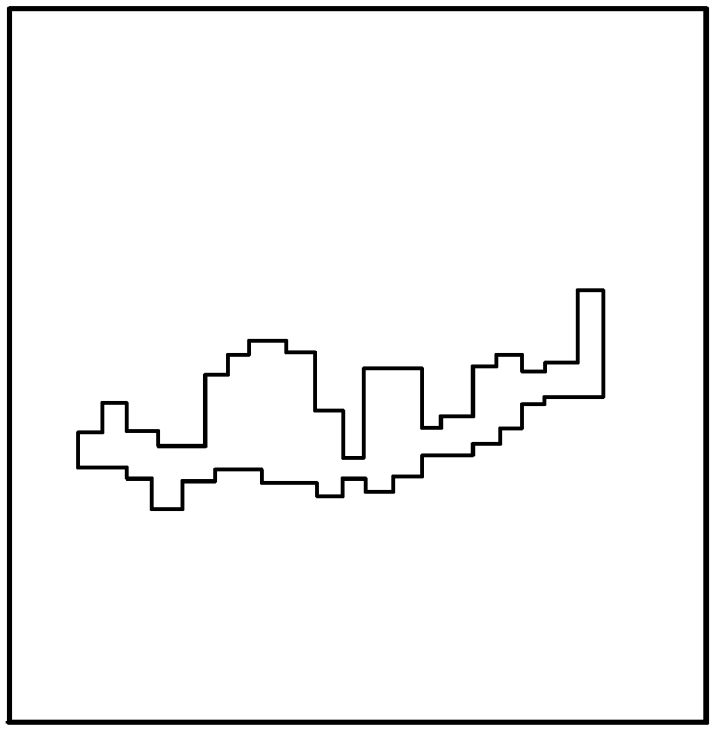
Figure 9A:
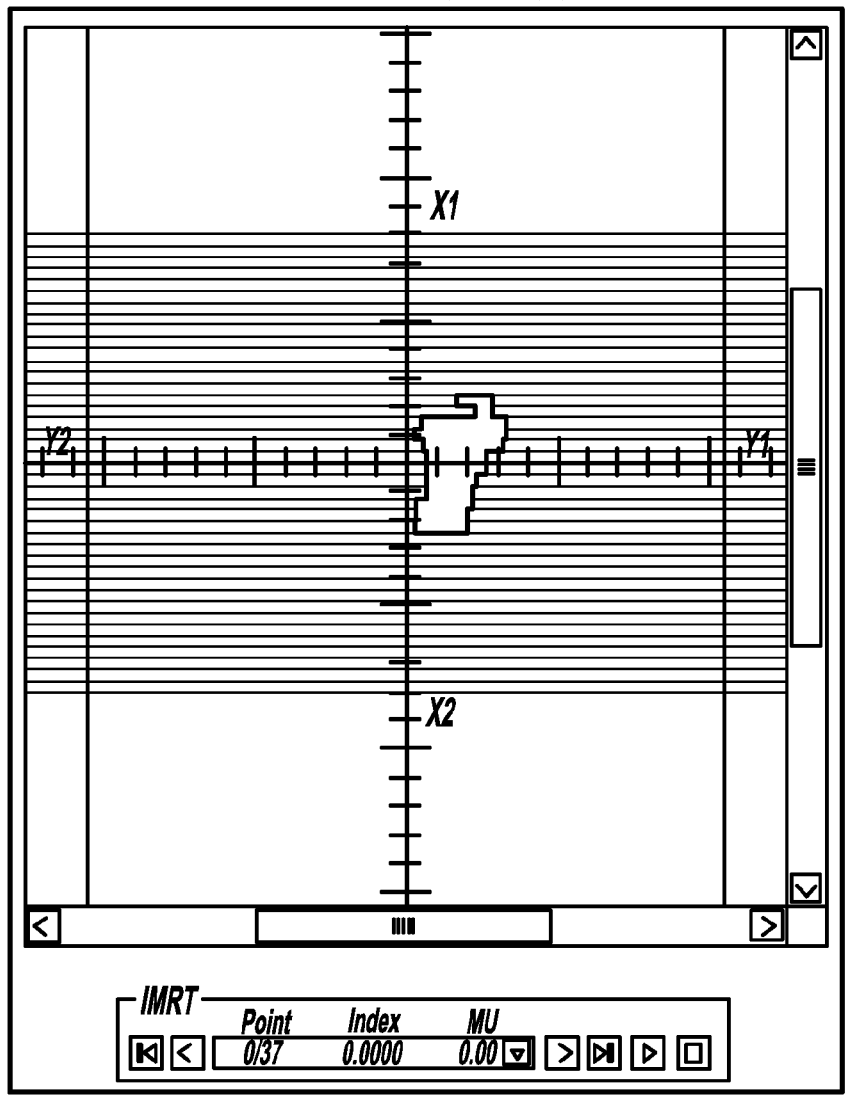
FIGS. 9a-c show real time kV plus MeV portal verification images in accordance with the invention.
Figure 9B:
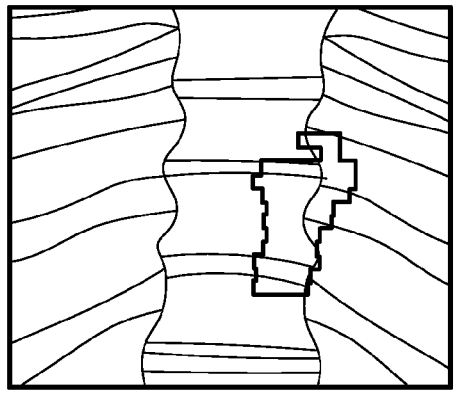
Figure 9C:
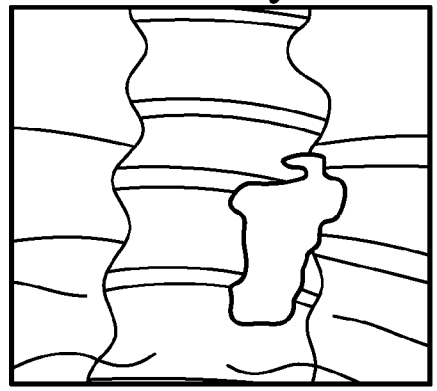
Figure 10:
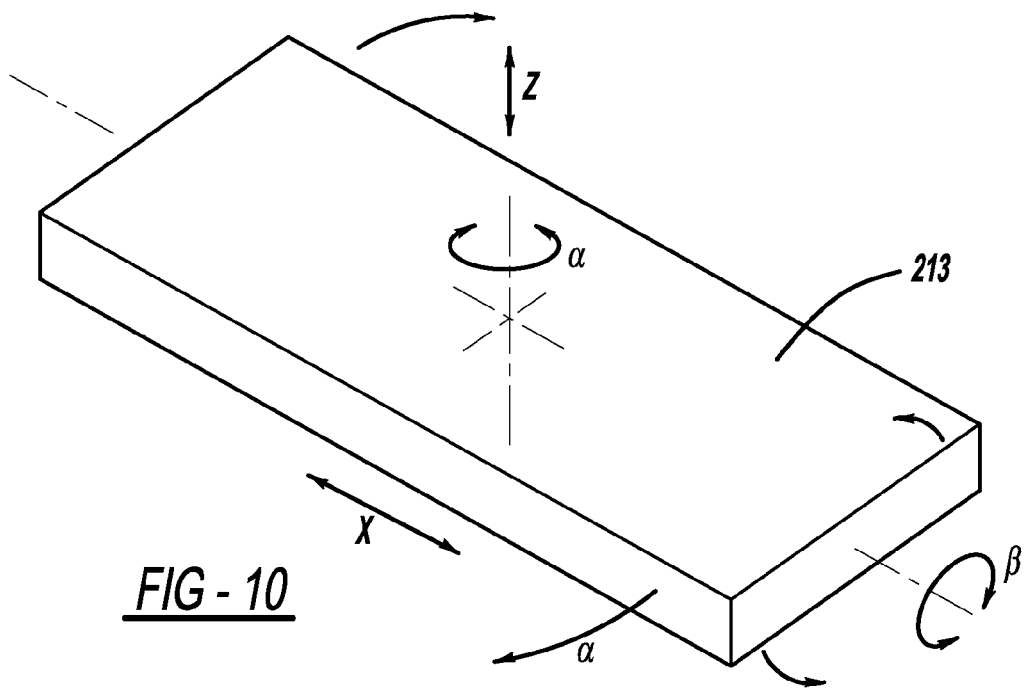
FIGS. 10 through 14 show a table to be used with the radiation therapy system of FIG. 1 in accordance with another embodiment of the invention.
Figure 11:
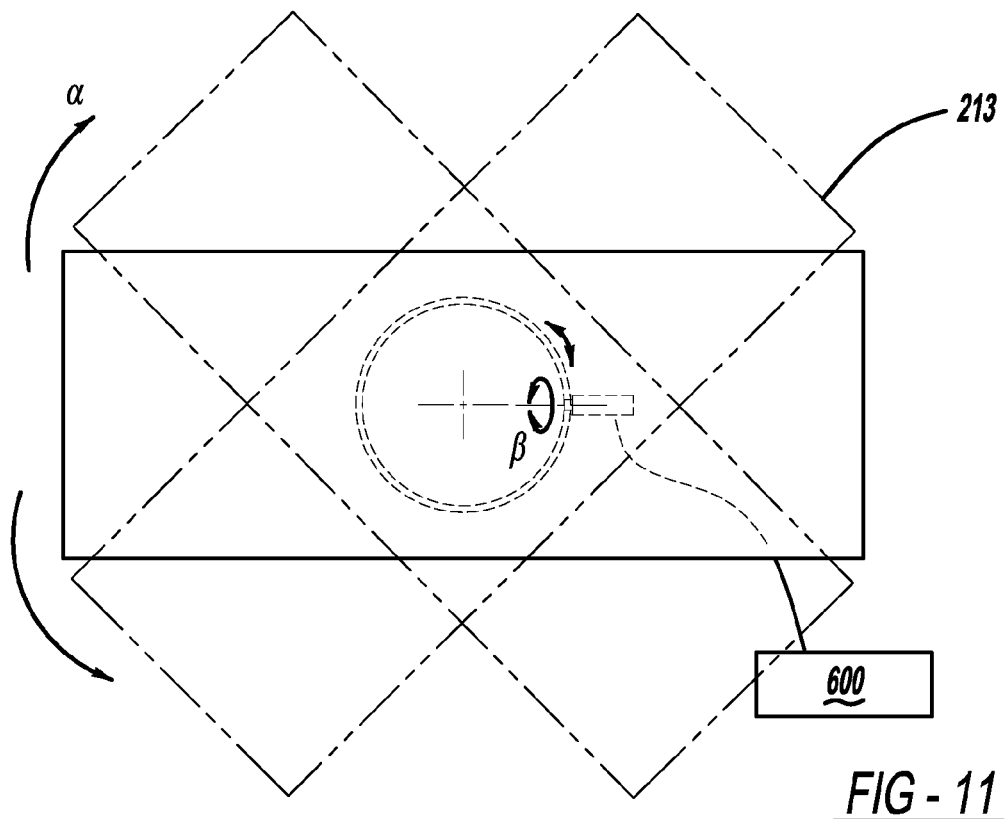
Figure 12:
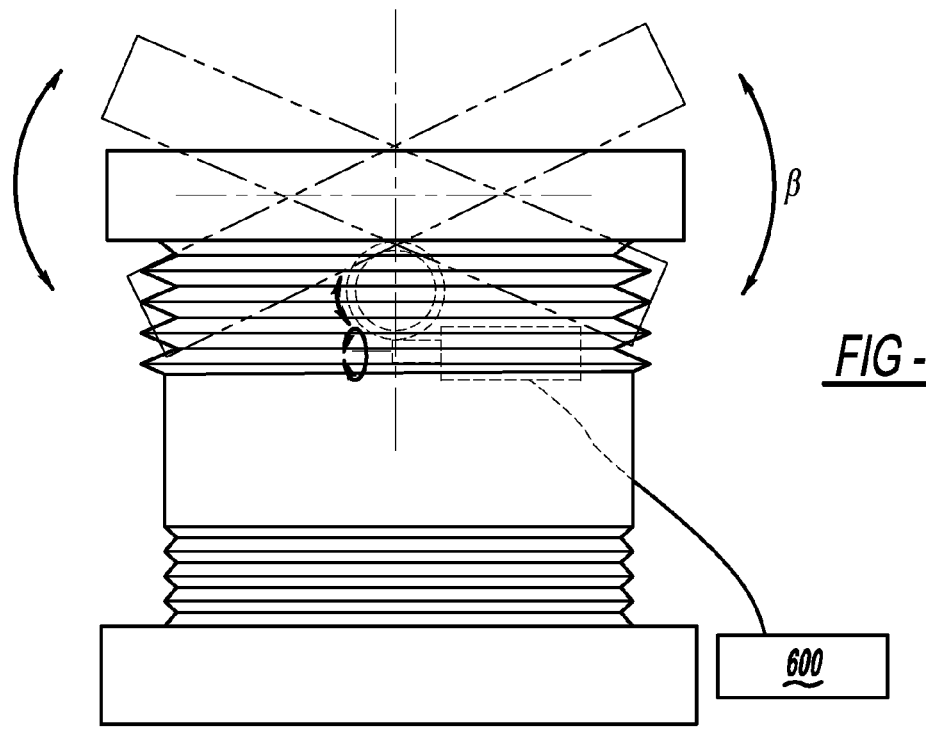
Figure 13:
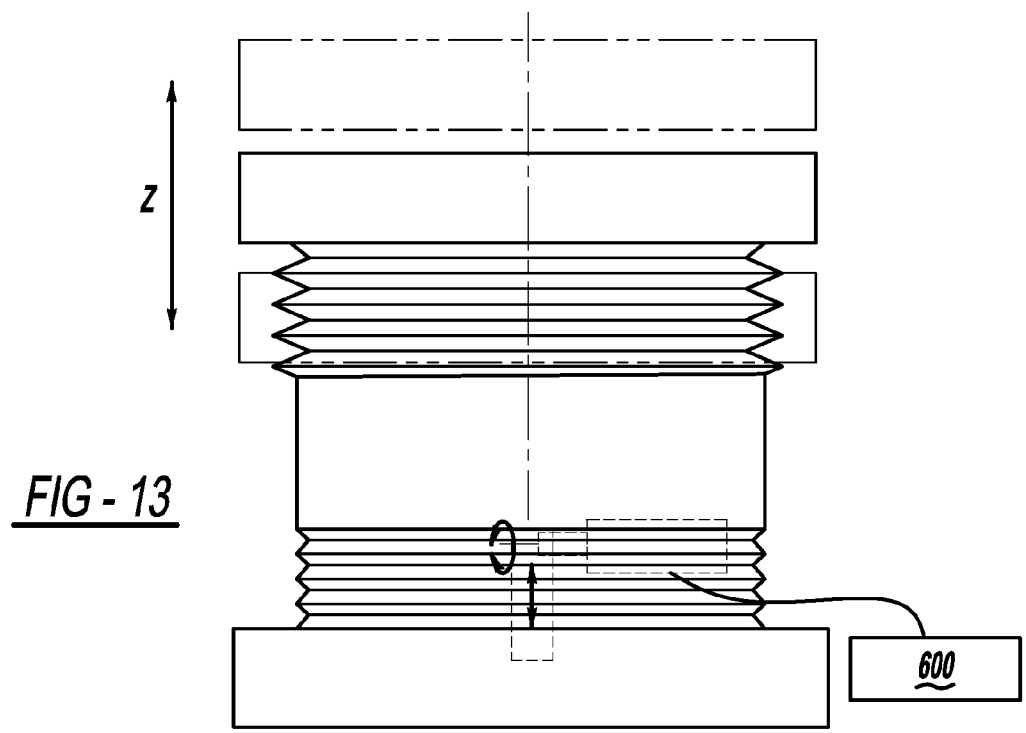
Figure 14:
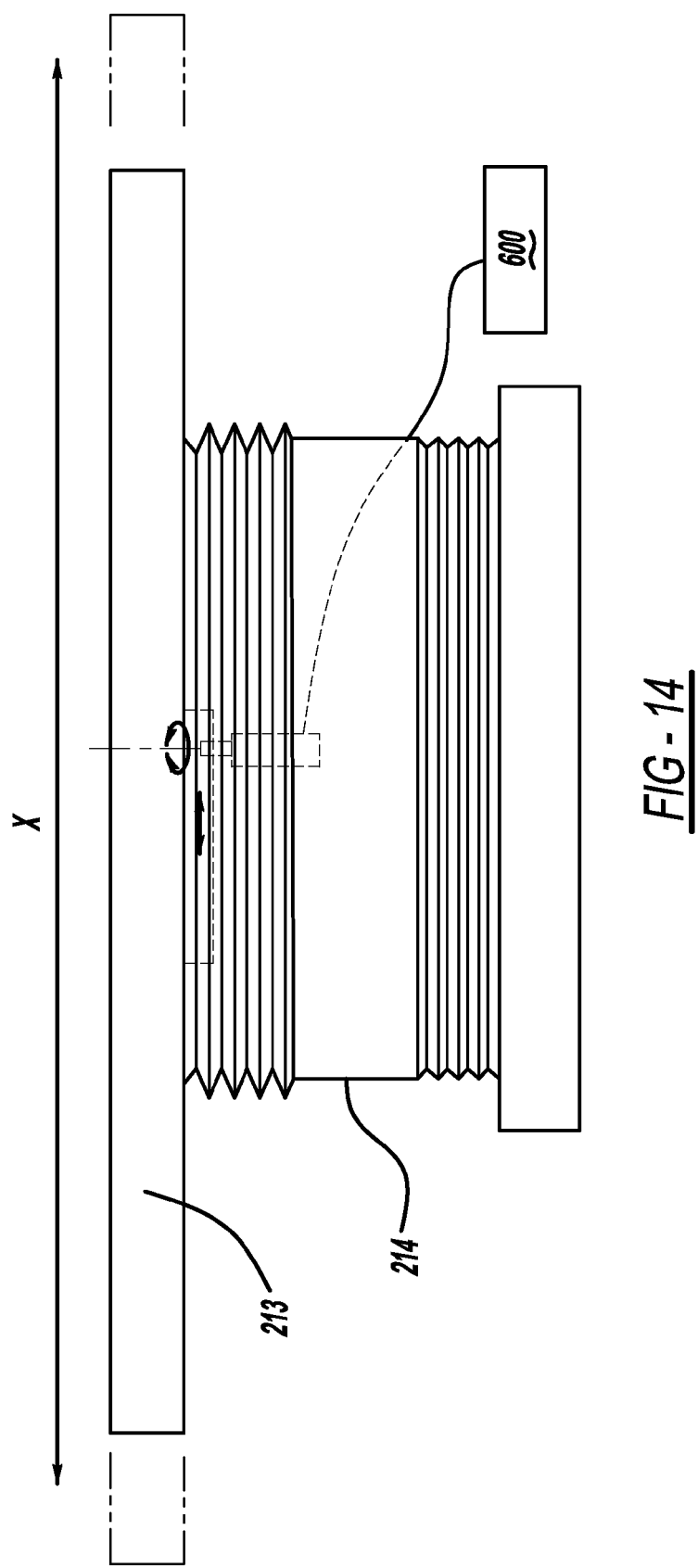

Shown in FIGS. 8 and 9 are images obtained with the system 100 employing of the process 1000 of FIG. 7. In particular, FIGS. 8a-c show real time imaging with verification and dose construction with the use the radiotherapy system 100; FIGS. 9b shows real time kV and MeV portal verification reference image, and FIG. 9c shows real time kV and MeV portal verification portal image.

Referring now to FIGS. 10 through 14, in various implementations, the table 211 includes a table top 213 that is positioned on top of a base 215. The base 215 is connected to a control system such as, for example, the treatment dose tracking and feedback system 600. The system 600 sends signals to the base to move the table in the x direction as well as up and down in the z direction for optimal treatment and imaging of the patient. Under the direction of the system 600, the table top 213 may also have a roll degree of freedom β to enable it to rotate about the y-axis, for example, about ±30°. In particular implementations, the table 213 also has a yaw degree of freedom a to enable it to rotate about the z-axis, which provides an improvement to intensity modulated arc therapy.

Yaw rotation about the z axis provides radiotherapy to certain difficult areas of a patient's anatomy such as the top of the patient's head, the prostate area, or the patient's breast. A movable table with linear and rotational motion also provides particular advantages in radiation therapy using therapy sources that are difficult to move, such as proton sources. In another implementation the patient sits in a chair which can be rotated in response to a fixed source.

The following is an example of volumetric modulated ARC therapy using couch rotation (i.e. a table 213 with rotational motion about the yaw axis) for an accelerated partial breast irradiation planning study.

In accelerated partial breast irradiation (APBI), beams are normally positioned tangent to the patient and not in the gantry plane of rotation in order to limit dose to critical structures such as the lung and contralateral breast. In this example, this principle was applied to volumetric arc therapy (VMAT) for APBI by creating arcs through couch rotation.

Seven previously delivered 3D conformal radiation therapy (3D-CRT) APBI plans were used as the basis for VMAT planning. Each 3D-CRT plan consisted of two medial and two lateral beams separated on each side by a median couch rotation of 45 degrees (range: 30-80 degrees). For the VMAT plan, two arcs were created, one medial and one lateral, using the same tangent gantry angle as the 3D-CRT plan and with the 3D-CRT couch positions taken as the extreme positions of the arcs. Control points were placed along the couch arc at five degree intervals, resulting in a median 23 (range: 18-24) control points per plan. VMAT plans were dosimetrically compared against both 3D-CRT and a 25-segment IMRT plan generated using the 3D-CRT beam arrangement. DVH values used for comparison included PTV_EVAL V95, mean lung dose, and conformality (defined as total V95/PTV_EVAL V95).

Compared to 3D-CRT, the VMAT plans significantly reduced mean lung doses by 18±16% (p=0.03) and had significantly better conformality (p=0.03). There was no significant difference between IMRT and VMAT plans in target coverage, conformality, and lung dose. In our study, IMRT had lower maximum doses, with a mean of 4070±40 cGy compared with 4150±50 cGy for VMAT (p=0.001), while VMAT plans used significantly fewer monitor units (MU), with a mean of 470±30 MU compared with 550±50 MU for IMRT (p=0.006).

Accordingly, a method for planning APBI using VMAT with couch rotation is provided. The resulting plans were comparable to IMRT in terms of dosimetric advantage relative to 3D-CRT while using fewer monitor units than IMRT.

Other embodiments are within the following claims.

What is claimed is:

1. A system for radiotherapy comprising:
 a first imaging system that generates projection images of an area of interest of an object;
 a second imaging system that generates portal images of the area of interest of the object synchronously with the generation of the projection images; and
 a processing system that receives data associated with the projection images and data associated with the portal images and reconstructs 3D and 4D portal images from the projection images and the portal images.

2. The system of claim 1, wherein the first imaging system includes an x-ray source that emits x-rays towards the object, and a detector that receives x-rays penetrating through the area of interest of the object and generates signals for the generation of the projection images of the area of interest of the object.

3. The system of claim 2, wherein the first imaging system includes a cone-beam computed tomography system, wherein the detector receives fan-shaped x-rays after they pass through the area of interest of the object, the detector generating an imaging signal for each of the received fan-shaped x-rays.

4. The system of claim 3, wherein the x-ray source includes a kV x-ray source.

5. The system of claim 1, wherein the second imaging system includes a radiation therapy source.

6. The system of claim 5, wherein the radiation therapy source generates a beam with an energy ranging from about 4 MeV to about 25 MeV.

7. The system of claim 5, wherein the second imaging system includes an imager that receives a beam emitted by the radiation therapy source and transmitted through the area of interest of the object to generate the portal images.

8. The system of claim 7, wherein the processing system provides feedback to the second imaging system to control the beam to provide a dynamic delivery control process for the treatment of the area of interest of the object.

9. The system of claim 8, wherein the output from the radiation therapy source is varied.

10. The system of claim 8, wherein the shape of the beam is varied.

11. The system of claim 1 further comprising a table upon which the object is positioned.

12. The system of claim 11, wherein the table has multiple degrees of freedom.

13. The system of claim 12, wherein one degree of freedom is along an x-axis.

14. The system of claim 13, wherein a second degree freedom is a roll degree of freedom about the x-axis.

15. The system of claim 11, wherein one degree of freedom is along a z-axis.

16. The system of claim 15, wherein a second degree of freedom is a yaw degree of freedom about the z-axis.

17. The system of claim 12, wherein a first degree of freedom is along an x-axis, a second degree of freedom is a roll degree of freedom about the x-axis, a third degree of freedom is along a z-axis, and a fourth degree of freedom is a yaw degree of freedom about the z-axis.

18. A method for radiotherapy comprising;
 generating projection images of an area of interest of an object with a first imaging system;
 generating portal images of the area of interest of the object with a second imaging system synchronously with the generation of the projection images; and
 receiving data associated with the projection images and data associated with the portal images and reconstructing 3D and 4D portal images from the projection images and the portal images with a processing system.

19. The method of claim 18, wherein the first imaging system includes a radiation source that emits kV radiation, and the second imaging system includes a therapy radiation source that emits a beam with MeV energy.

20. The method of claim 18 wherein the processing system provides feedback to the second imaging system to control the beam to provide a dynamic delivery control process for the treatment of the area of interest of the object.

* * * * *